United States Patent
Sugimoto et al.

(10) Patent No.: US 9,752,996 B2
(45) Date of Patent: Sep. 5, 2017

(54) X-RAY INSPECTION DEVICE

(71) Applicant: ISHIDA CO., LTD., Kyoto-shi, Kyoto (JP)

(72) Inventors: Kazuyuki Sugimoto, Ritto (JP); Osamu Hirose, Ritto (JP)

(73) Assignee: ISHIDA CO., LTD., Kyoto (JP)

( * ) Notice: Subject to any disclaimer, the term of this patent is extended or adjusted under 35 U.S.C. 154(b) by 0 days.

(21) Appl. No.: 15/502,491

(22) PCT Filed: Aug. 5, 2015

(86) PCT No.: PCT/JP2015/072182
§ 371 (c)(1),
(2) Date: Feb. 7, 2017

(87) PCT Pub. No.: WO2016/024502
PCT Pub. Date: Feb. 18, 2016

(65) Prior Publication Data
US 2017/0227477 A1 Aug. 10, 2017

(30) Foreign Application Priority Data
Aug. 11, 2014 (JP) .................. 2014-163968

(51) Int. Cl.
*G01N 23/00* (2006.01)
*G01N 23/18* (2006.01)
*G01N 23/04* (2006.01)

(52) U.S. Cl.
CPC ............. *G01N 23/18* (2013.01); *G01N 23/04* (2013.01); *G01N 2223/206* (2013.01); *G01N 2223/618* (2013.01); *G01N 2223/643* (2013.01)

(58) Field of Classification Search
CPC ................. G01N 2223/643; G01N 23/087
See application file for complete search history.

(56) References Cited

U.S. PATENT DOCUMENTS

2013/0195244 A1* 8/2013 Hosokawa ............. G01N 23/04
378/53
2014/0294151 A1* 10/2014 Suyama ............... G01N 23/083
378/62

FOREIGN PATENT DOCUMENTS

JP 2012-078254 A 4/2012
JP 2012-088291 A 5/2012
(Continued)

OTHER PUBLICATIONS

The Decision of Grant from the corresponding Japanese Patent Application No. 2014-163968 dated Jan. 12, 2016.
(Continued)

*Primary Examiner* — Dani Fox
(74) *Attorney, Agent, or Firm* — Shinjyu Global IP

(57) ABSTRACT

Provided is a highly reliable X-ray inspection device having two line sensors, in which accurate inspection results can be obtained even when there is displacement of the mounting position of the line sensors. The X-ray inspection device is provided with a conveyor unit for conveying an article, an X-ray emitter, a first line sensor, a second line sensor, a detection unit, and a corrected-image generation unit. The X-ray emitter emits X-rays to the article conveyed by the conveyor unit. The first line sensor detects, in a low energy band, X-rays that have passed through the article. The second line sensor detects, in a high energy band, X-rays that have passed through the article. The detection unit detects positional displacement of the second line sensor with respect to the first line sensor in horizontal direction and vertical direction.

9 Claims, 13 Drawing Sheets

(56) References Cited

FOREIGN PATENT DOCUMENTS

| JP | 2012-194101 A | 10/2012 |
|---|---|---|
| JP | 2013-068518 A | 4/2013 |
| JP | 2013-088143 A | 5/2013 |
| JP | 2013-101041 A | 5/2013 |

OTHER PUBLICATIONS

The Search Report from the corresponding International Patent Application No. PCT/JP2015/072182 dated Oct. 27, 2015.
The Preliminary Report on Patentability with Written Opinion from the corresponding International Patent Application No. PCT/JP2015/072182 dated Feb. 14, 2017.

\* cited by examiner

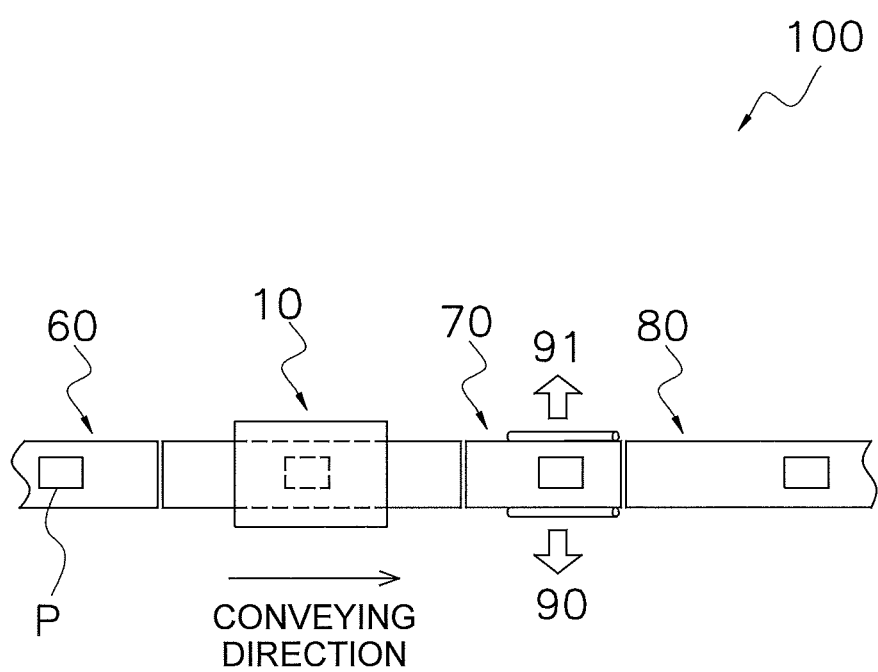
F I G. 1

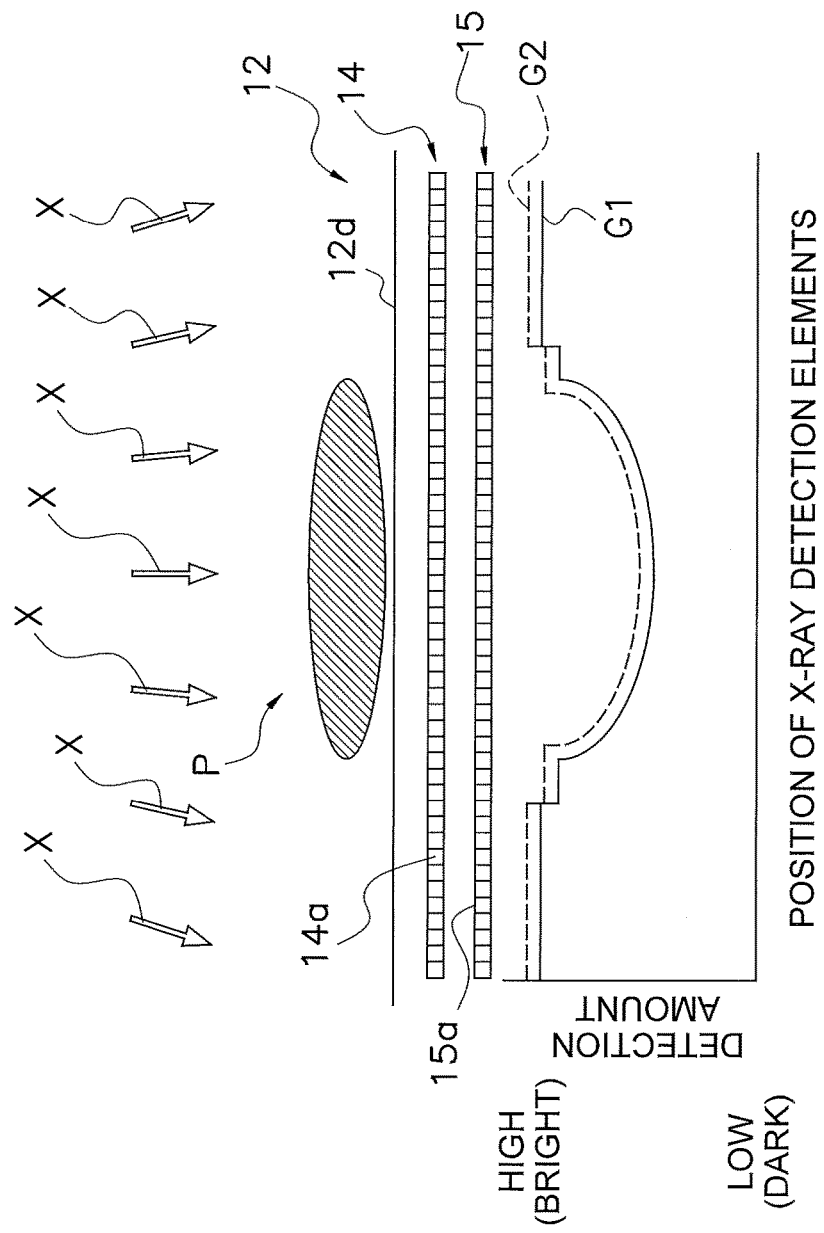
F I G. 4

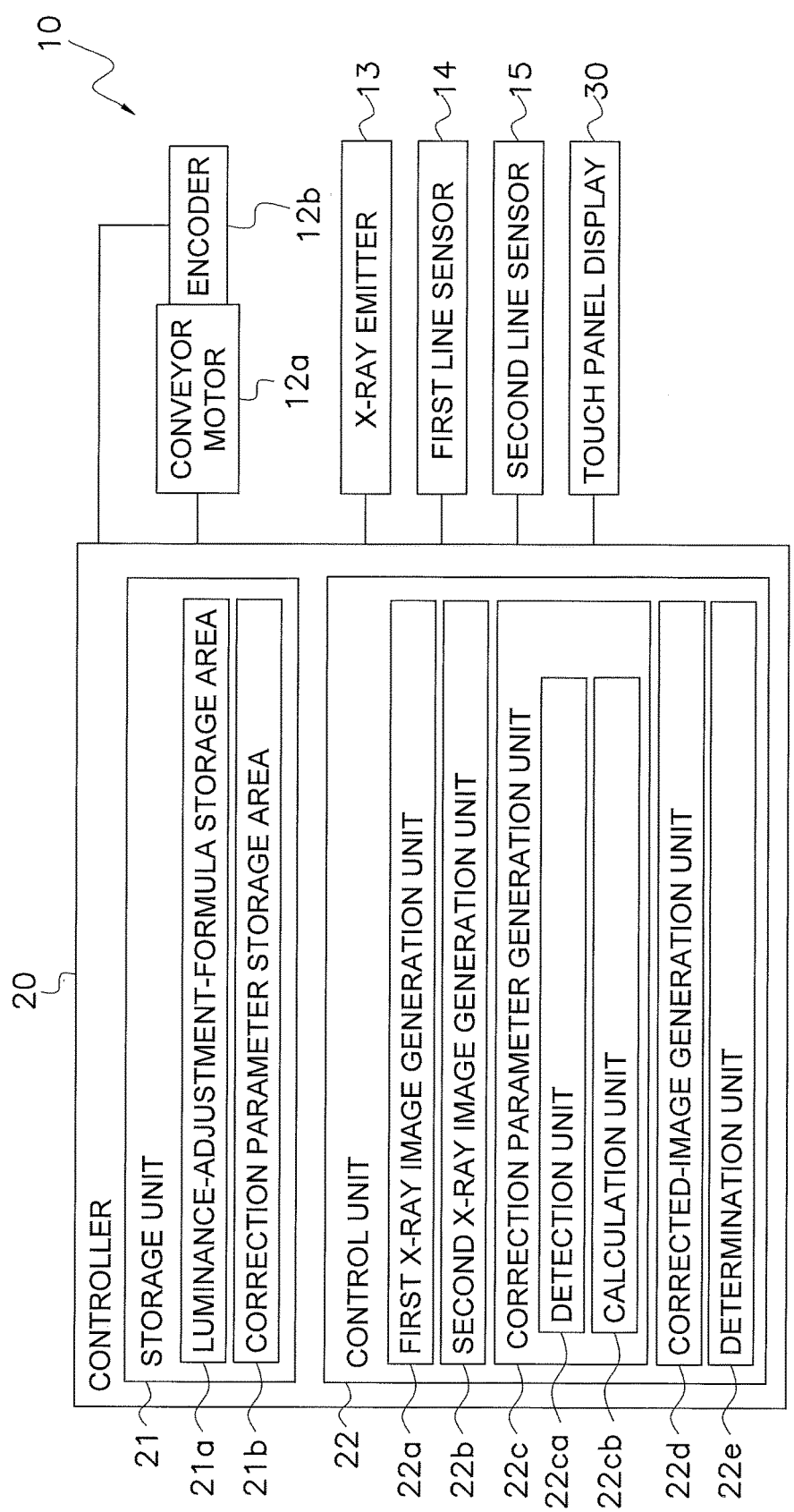
F I G. 5

FIG. 6
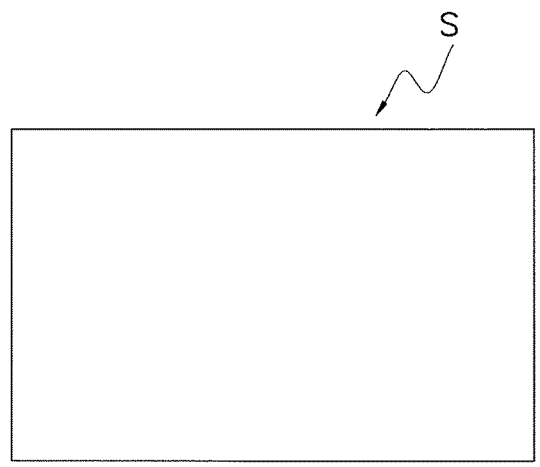
FIG. 7
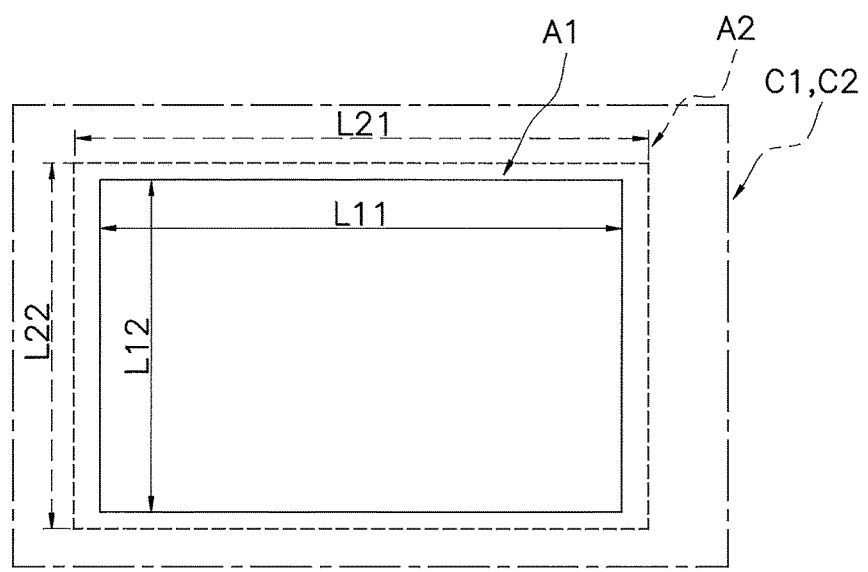
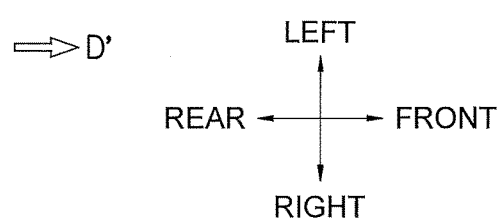

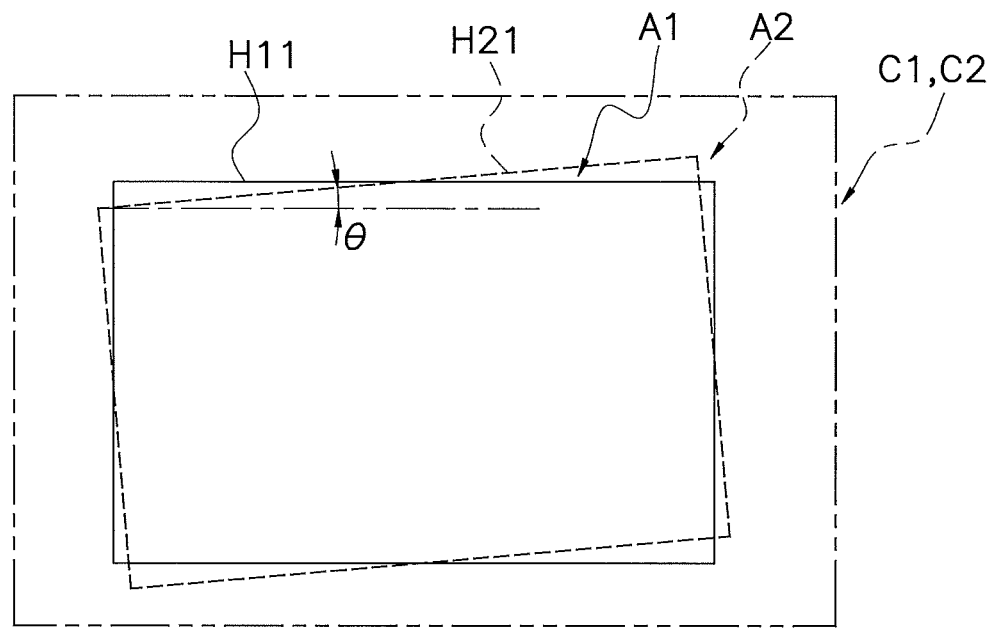
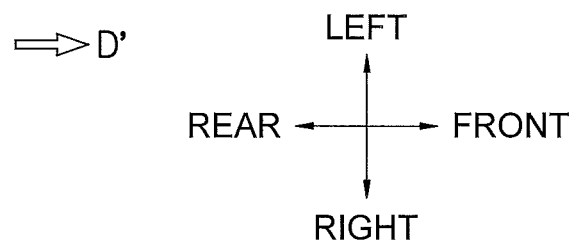
FIG. 8

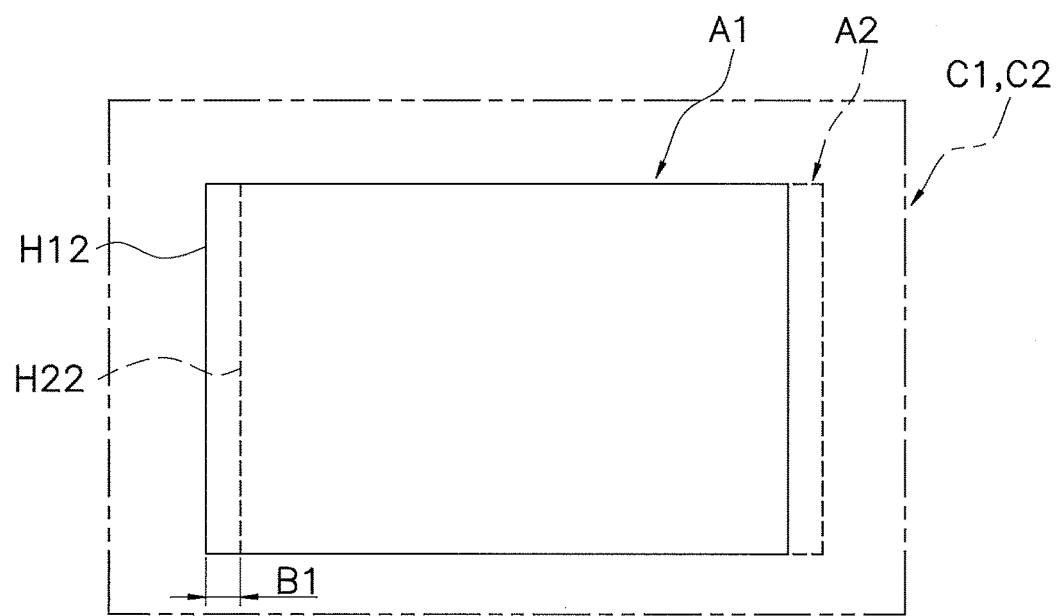
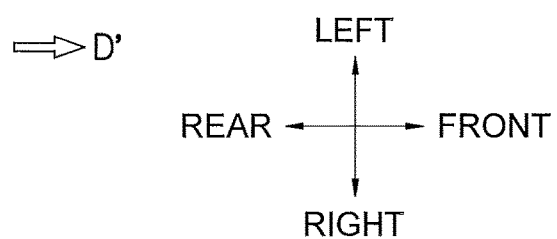
FIG. 9

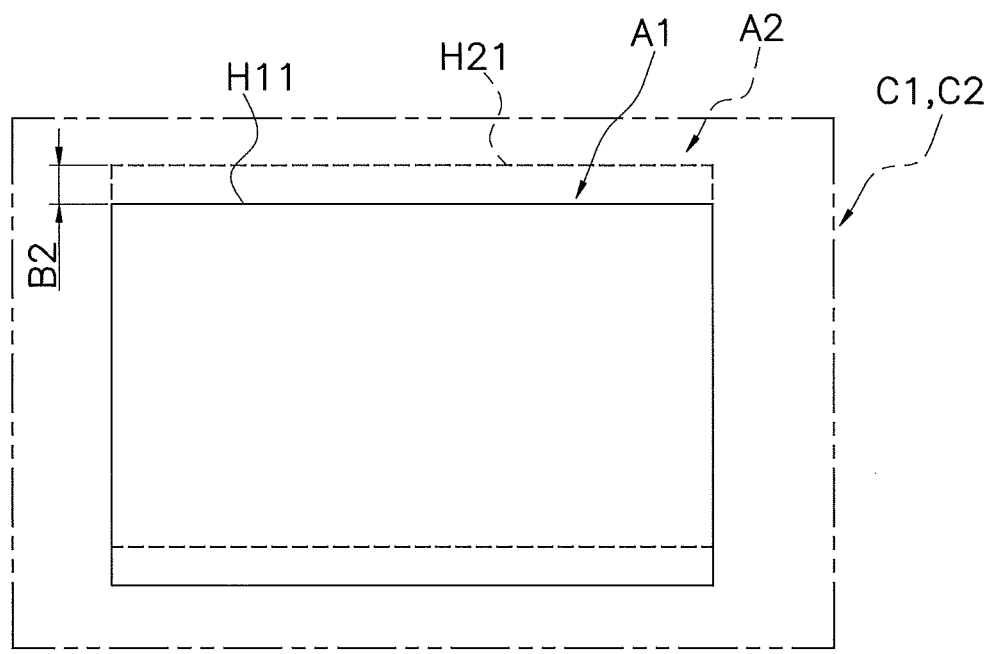
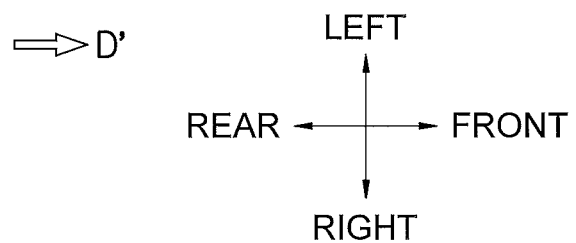
FIG. 10

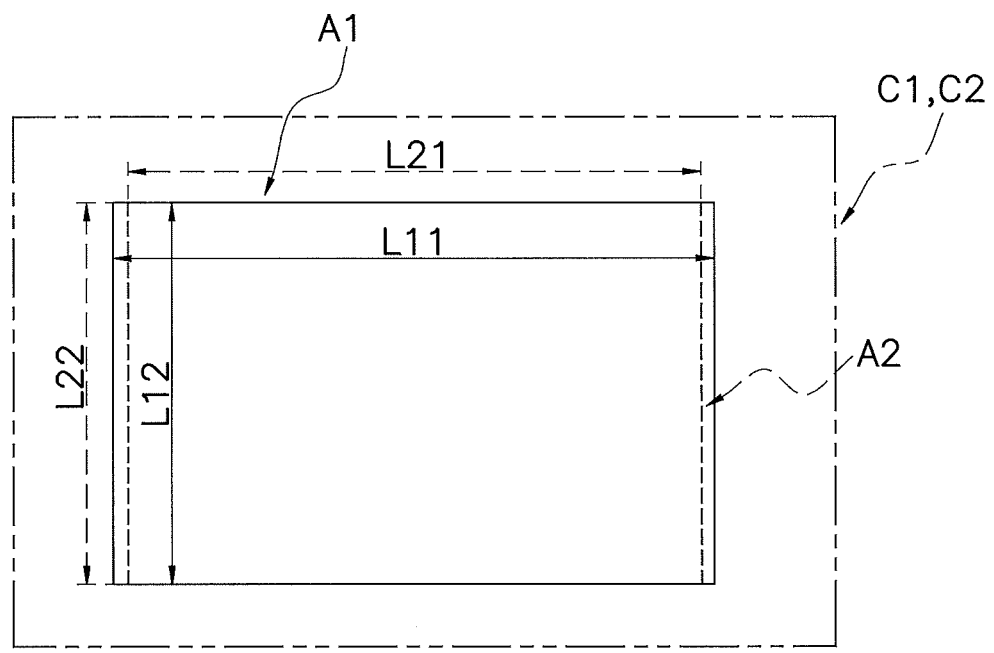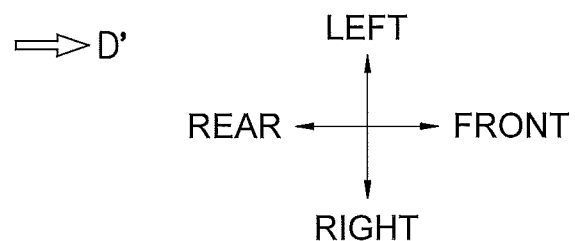
FIG. 11

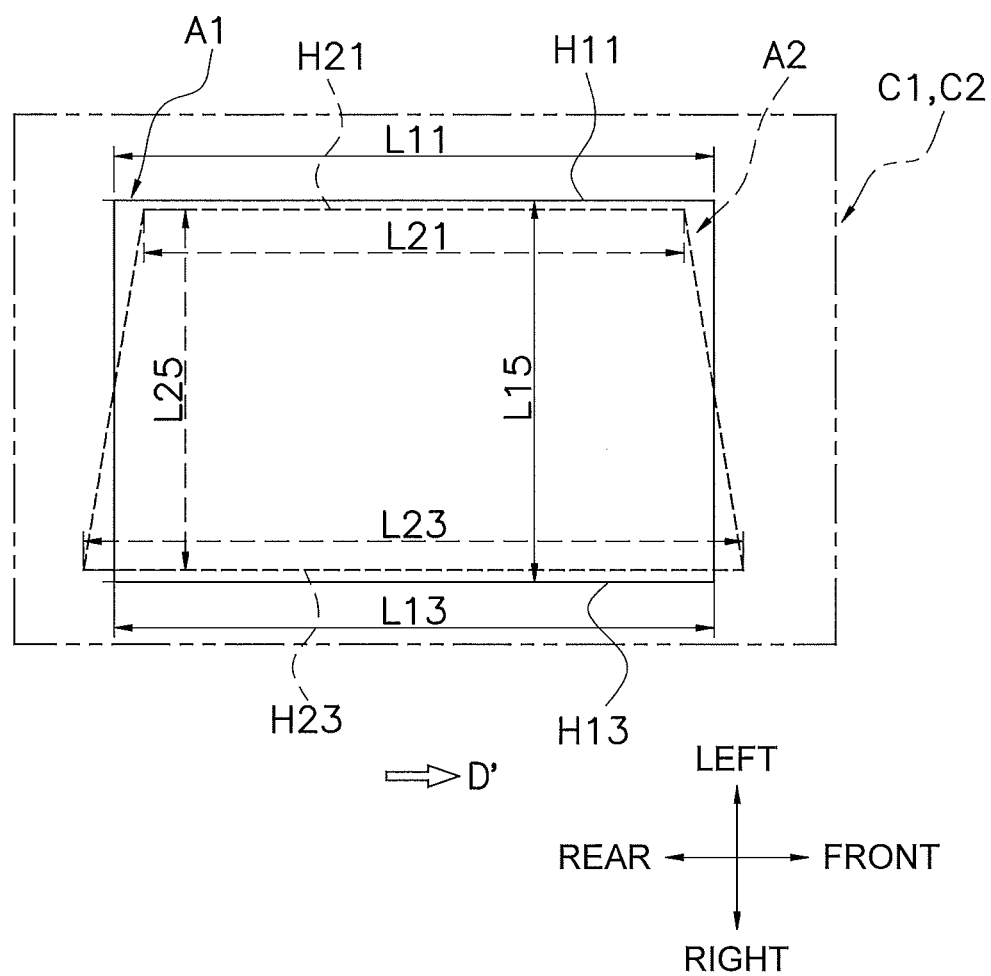
F I G. 1 2

FIG. 13C
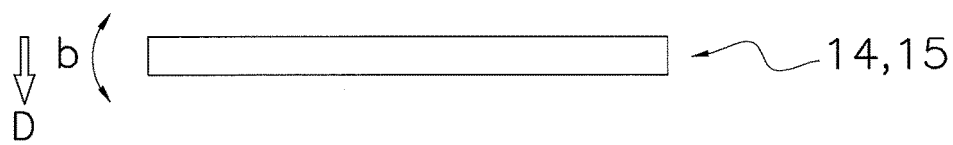
FIG. 14
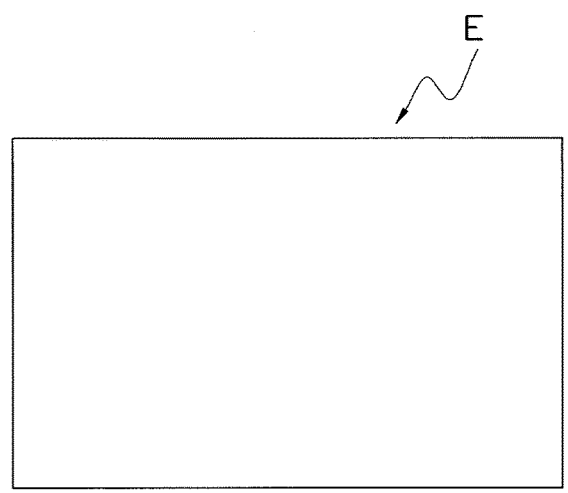
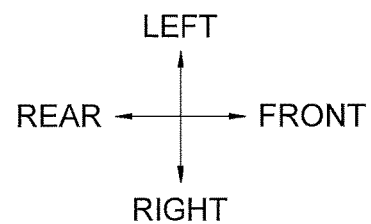

X-RAY INSPECTION DEVICE

PRIORITY

This is a National Stage application under 35 U.S.C. §371 of International Application PCT/JP2015/072182, with an international filing date of Aug. 5, 2015, which claims priority to Japanese Patent Application No. 2014-163968 filed on Aug. 11, 2014. The entire disclosures of International Application PCT/JP2015/072182 and Japanese Patent Application No. 2014-163968 are hereby incorporated herein by reference.

TECHNICAL FIELD

Certain implementations of the present invention relate to an X-ray inspection device, and more particularly an X-ray inspection device having two line sensors.

BACKGROUND

There are known, in the art, X-ray inspection devices that are provided with two line sensors and that acquire an X-ray image of an individual energy band with each line sensor, and perform various inspections using a difference image of two X-ray images acquired (e.g. Patent Literature 1 (Japanese Patent Application Laid-open No. 2012-078254)).

In such X-ray inspection devices, mounting positions of the two line sensors are designed so that a suitable difference image is obtained from X-ray images acquired by the two line sensors. In other words, mounting positions of the two line sensors are designed so as to be capable of accurately associating two X-ray images in order to perform difference processing between pixels based on the detection results of X-rays that have passed through the same position of an inspection object in the two X-ray images acquired from the detection results of the two line sensors.

SUMMARY

However, mounting of the line sensors requires high precision, and therefore, the actual mounting position of the line sensors may be displaced from the designed predetermined position. In such a case, direct usage of the two acquired X-ray images does not allow an accurate differential image to be obtained, and the inspection precision of the X-ray inspection device is reduced.

One possible measure to prevent such a problem involves strictly managing the assembly process of the X-ray inspection device. Nevertheless, although the occurrence of displacement of the mounting position of the line sensors can be minimized as long as the assembly process is strictly controlled, increment of the number of man-hours for assembly process or the like is incurred because of the request for strict control of the assembly process.

An object of certain implementations of the present invention is to provide a highly reliable X-ray inspection device having two line sensors, in which accurate inspection results can be obtained even when there is displacement of the mounting position of the line sensors.

An X-ray inspection device according to a first aspect of the present invention is provided with a conveying means, an X-ray source, a first line sensor, a second line sensor, a detection unit, and a corrected-image generation unit. The conveying means is configured to convey an article. The X-ray source is configured to emit X-rays to the article, which is conveyed by the conveying means. The first line sensor is configured to detect X-rays that have passed through the article in a first energy band. The second line sensor is configured to detect X-rays that have passed through the article in a second energy band which is different from the first energy band. The detection unit is configured to detect positional displacement of the second line sensor with respect to the first line sensor at least one direction of horizontal direction and vertical direction. The corrected-image generation unit is configured to generate, based on the detection results of the detection unit, a corrected second X-ray image by correcting a second X-ray image of the article obtained based on the detection results of the second line sensor.

In the X-ray inspection device according to the first aspect, positional displacement of the second line sensor with respect to the first line sensor in the horizontal and/or vertical direction is detected, and the second X-ray image obtained from the detection results of the second line sensor is corrected based on the displacement. For this reason, accurate inspection results can be obtained even when displacement is occurred in the mounting position of the line sensors. In other words, a highly reliable X-ray inspection device being capable of obtaining accurate inspection results is realized regardless of displacement of the mounting position of the second line sensor with respect to the first line sensor.

An X-ray inspection device according to a second aspect of the present invention is the X-ray inspection device according to the first aspect, wherein the second line sensor is arranged below the first line sensor. The second energy band is higher than the first energy band in energy.

In the X-ray inspection device according to the second aspect, because the first line sensor is arranged above the second line sensor, articles (obstacles) through which the X-rays from the X-ray source pass before reaching the first line sensor is fewer than articles through which the X-rays from the X-ray source pass before reaching the second line sensor. For this reason, the first X-ray image is clearer than the second X-ray image. Here, because the first X-ray image, which is clearer than the second X-ray image, is used as a reference, positional displacement of the second line sensor with respect to the first line sensor can be readily and accurately obtained.

An X-ray inspection device according to a third aspect of the present invention is the X-ray inspection device according to the first or second aspect, wherein the detection unit is configured to detect positional displacement of the second line sensor with respect to the first line sensor in advance based on the detection result of the first line sensor and the second line sensor of the X-rays which have been emitted from the X-ray source to a sample having a known shape, which is conveyed by the conveying means, and have passed through the sample.

In the X-ray inspection device according to the third aspect, the positional displacement of the second line sensor with respect to the first line sensor can be more accurately detected using an X-ray image of a sample having a known shape.

An X-ray inspection device according to a fourth aspect of the present invention is the X-ray inspection device according to any of the first to third aspects, wherein the detection unit is configured to detect the horizontal-direction tilt of the second line sensor with respect to the first line sensor. The corrected-image generation unit is configured to generate the corrected second X-ray image by rotating the second X-ray image.

According to the aspect described above, the corrected second X-ray image can be generated by correcting the second X-ray image with image processing and accurate inspection results thereby can be obtained, even when horizontal-direction tilt (rotational displacement of the position in the horizontal direction) of the second line sensor with respect to the first line sensor is occurred.

An X-ray inspection device according to a fifth aspect of the present invention is the X-ray inspection device according to any of the first to third aspects, wherein the detection unit is configured to detect displacement of the second line sensor with respect to the first line sensor to an upstream side or a downstream side in the conveying direction of the conveying means. The corrected-image generation unit is configured to generate the corrected second X-ray image by moving the second X-ray image in a direction that corresponds to the upstream side or the downstream side in the conveying direction.

According to the aspect described above, the corrected second X-ray image can be generated by correcting the second X-ray image with image processing and accurate inspection results thereby can be obtained, even when displacement of the second line sensor with respect to the first line sensor is occurred to the upstream side or downstream side in the conveying direction.

An X-ray inspection device according to a sixth aspect of the present invention is the X-ray inspection device according to any of the first to third aspects, wherein the detection unit is configured to detect displacement of the second line sensor with respect to the first line sensor in a direction orthogonal to the conveying direction of the conveying means as viewed from above. The corrected-image generation unit is configured to generate the corrected second X-ray image by moving the second X-ray image in a direction that corresponds to the direction orthogonal to the conveying direction.

According to the aspect described above, the corrected second X-ray image can be generated by correcting the second X-ray image with image processing and accurate inspection results thereby can be obtained, even when displacement of the second line sensor with respect to the first line sensor is occurred in the lateral direction perpendicular to the conveying direction.

An X-ray inspection device according to a seventh aspect of the present invention is the X-ray inspection device according to any of the first to third aspects, wherein the detection is configured to detect the vertical-direction tilt of the second line sensor with respect to the first line sensor. The corrected-image generation unit is configured to generate the corrected second X-ray image by enlarging the second X-ray image at one end side and reducing the second X-ray image at the other end side in a direction that corresponds to the tilt direction of the second line sensor.

According to the aspect described above, the corrected second X-ray image can be generated by correcting the second X-ray image with image processing and accurate inspection results thereby can be obtained, even when the second line sensor is tilted with respect to the first line sensor in the vertical direction.

An X-ray inspection device according to an eighth aspect of the present invention is the X-ray inspection device according to any of the first to third aspects, wherein the detection unit is configured to detect the vertical-direction tilt of the second line sensor with respect to the first line sensor. The corrected-image generation unit is configured to generate the corrected second X-ray image by enlarging or reducing the second X-ray image in a direction that corresponds to the tilt direction of the second line sensor.

According to the aspect described above, the corrected second X-ray image can be generated by correcting the second X-ray image with image processing and accurate inspection results thereby can be obtained, even when the second line sensor is tilted with respect to the first line sensor in the vertical direction.

An X-ray inspection device according to a ninth aspect of the present invention is the X-ray inspection device according to any of the first to third aspects, wherein the detection unit is configured to detect vertical-direction displacement of the second line sensor with respect to the first line sensor. The corrected-image generation unit is configured to generate the corrected second X-ray image by enlarging or reducing the second X-ray image.

According to the aspect described above, the corrected second X-ray image can be generated by correcting the second X-ray image with image processing and accurate inspection results thereby can be obtained, even when the second line sensor is displaced in the vertical direction with respect to the first line sensor.

In the X-ray inspection device according to an implementation of the present invention, positional displacement of the second line sensor with respect to the first line sensor in the horizontal and/or vertical direction is detected, and the second X-ray image obtained from the detection results of the second line sensor is corrected based on the displacement. For this reason, accurate inspection results can be obtained even when displacement is occurred in the mounting position of the line sensors. In other words, a highly reliable X-ray inspection device being capable of obtaining accurate inspection results is realized regardless of displacement of the mounting position of the second line sensor with respect to the first line sensor.

BRIEF DESCRIPTION OF THE DRAWINGS

FIG. 1 is a schematic view of an inspection system including an X-ray inspection device according to an embodiment of the present invention;

FIG. 4 is an example of a graph showing the amount of transmitted X-rays detected by the two line sensors provided to the X-ray inspection device of FIG. 2;

FIG. 5 is a block diagram of the X-ray inspection device of FIG. 2;

FIG. 6 is an example of a sample used when positional displacement of the second line sensor with respect to the first line sensor is to be detected;

FIG. 7 is an example of a drawing depicting superimposingly the first image and second image created for the sample of FIG. 6, and shows the first and second images obtained when the second line sensor is displaced in the vertical direction with respect to the first line sensor;

FIG. 8 is an example of a drawing depicting superimposingly the first image and second image created for the sample of FIG. 6, and shows the first and second images obtained when the second line sensor is tilted in the horizontal direction with respect to the first line sensor;

FIG. 9 is an example of a drawing depicting superimposingly the first image and second image created for the sample of FIG. 6, and shows the first and second images obtained when the second line sensor is displaced in the conveying direction with respect to the first line sensor;

FIG. 10 is an example of a drawing depicting superimposingly the first image and second image created for the sample of FIG. 6, and shows the first and second images obtained when the second line sensor is displaced in the direction orthogonal to the conveying direction with respect to the first line sensor;

FIG. 11 is an example of a drawing depicting superimposingly the first image and second image created for the sample of FIG. 6, and shows the first and second images obtained when the second line sensor is tilted in the vertical direction along the conveying direction with respect to the first line sensor;

FIG. 12 is an example of a drawing depicting superimposingly the first image and second image created for the sample of FIG. 6, and shows the first and second images obtained when the second line sensor is tilted in the vertical direction along the direction orthogonal to the conveying direction with respect to the first line sensor;

FIG. 13C is a drawing illustrating the displacement direction of the second line sensor with respect to the first line sensor, and is a view of the first and second line sensors as viewed from above, the arrow D in the drawing indicating the conveying direction of the conveyor unit; and FIG. 14 is a drawing illustrating the direction used in the description of the process for generating a corrected second X-ray image.

DETAILED DESCRIPTION

The X-ray inspection device 10 according to an embodiment of the present invention is described below with reference to the drawings. The embodiment described below is a specific example of the present invention and does not limit the technical scope of the present invention.

(1) General Overview

Figure 2:
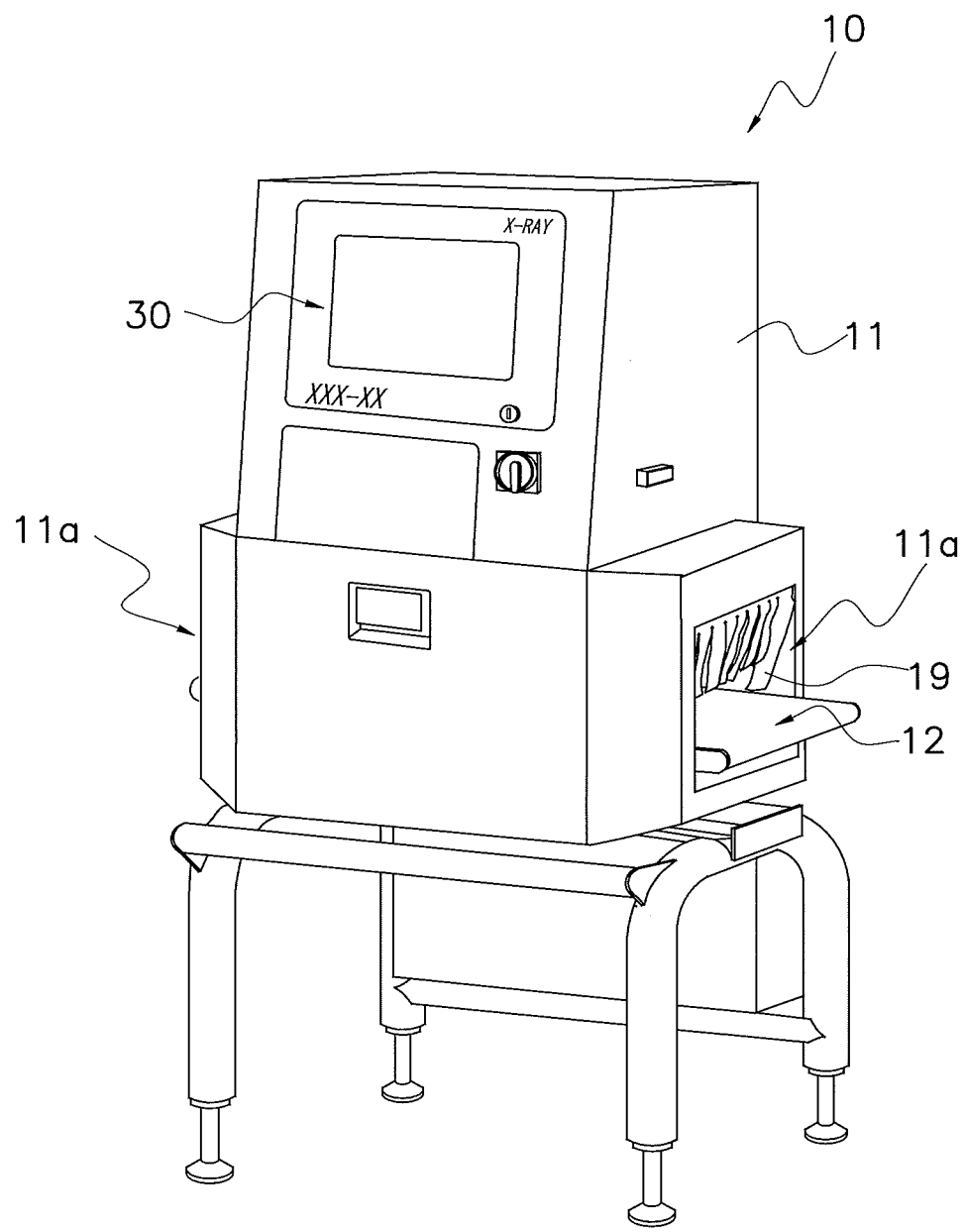
FIG. 2 is a perspective view of the external appearance of the X-ray inspection device of FIG. 1.

FIG. 1 is a schematic view of an inspection system 100 including the X-ray inspection device 10 according to an embodiment of the present invention. FIG. 2 is a perspective view of the external appearance of the X-ray inspection device 10 according to an embodiment of the present invention.

The X-ray inspection device 10 is incorporated into a production line for articles P such as a food product. The X-ray inspection device 10 inspects the quality of the article P by emitting X-rays to the article P, which is continuously conveyed. In particular, as quality inspection, the X-ray inspection device 10 inspects whether the article P is contaminated with foreign matter.

In the inspection system 100, the article P is conveyed by a pre-stage conveyor 60 to the X-ray inspection device 10 (see FIG. 1). In the X-ray inspection device 10, a foreign matter inspection is carried out for the article P, and the articles P are divided into defective and non-defective products. The results of the foreign matter inspection by the X-ray inspection device 10 are transmitted to a sorting mechanism 70 disposed on the downstream side of the X-ray inspection device 10 (FIG. 1). The sorting mechanism 70 sends the articles P determined to be non-defective in the X-ray inspection device 10 to a line conveyor 80 (FIG. 1). Also, the sorting mechanism 70 sends the articles P determined to be defective in the X-ray inspection device 10 to defective-product-holding conveyors 90, 91 (FIG. 1).

(2) Detailed Description

The X-ray inspection device 10 is mainly provided with a shield box 11 (see FIG. 2), a conveyor unit 12 (see FIG. 3), an X-ray emitter 13 (see FIG. 3), a first line sensor 14 (see FIG. 3), a second line sensor 15 (see FIG. 3), a touch panel display 30 (see FIG. 1), and a controller 20 (FIG. 5).

(2-1) Shield Box

The shield box 11 (see FIG. 2) is a casing of the X-ray inspection device 10. The conveyor unit 12, the X-ray emitter 13, the first line sensor 14, the second line sensor 15, and the controller 20 are accommodated in the shield box 11. The touch panel display 30, a key insertion opening, a power switch, and the like are disposed in the upper front part of the shield box 11.

Openings 11a for conveying articles P in and out of the shield box are formed in the side surfaces of the shield box 11 on the upstream side and downstream side in the conveying direction D (see FIG. 3) of the conveyor unit 12 (FIG. 2). The opening 11a is closed by a shield curtain 19 for minimizing X-ray leakage to the exterior of the shield box 11 (FIG. 2). The shield curtain 19 is made of tungsten-containing rubber. The shield curtain 19 is pushed away by an article P or a sample S (described hereunder) conveyed by the conveyor unit 12 when the article P or article S is conveyed into the shield box 11 or when the article P or sample S is conveyed out from the shield box 11.

(2-2) Conveyor Unit

The conveyor unit 12 is an example of conveying means for conveying an article P. The conveyor unit 12 is disposed so as to pass through the openings 11a formed in the both side surfaces of the shield box 11, as shown in FIG. 2.

Figure 3:
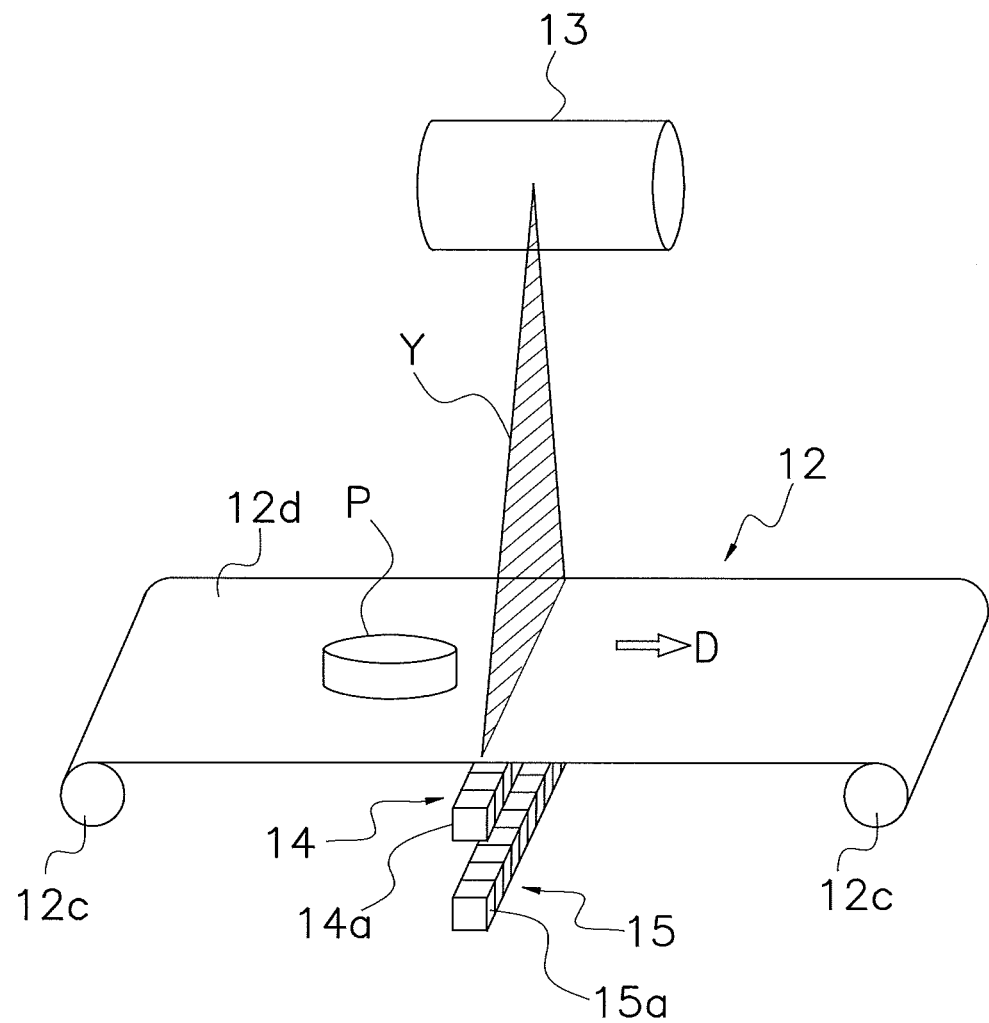
FIG. 3 is a simplified schematic view of the interior of a shield box of the X-ray inspection device of FIG. 2.

The conveyor unit 12 mainly has an inverter-type conveyor motor 12a (see FIG. 5), an encoder 12b (see FIG. 5), conveyor rollers 12c (see FIG. 3), and an endless belt 12d (see FIG. 3). The encoder 12b is mounted on the conveyor motor 12a. The conveyor rollers 12c are driven by the conveyor motor 12a. The conveyor rollers 12c are driven to rotate the belt 12d and convey the article P on the belt 12d downstream (toward the sorting mechanism 70 side). The later-described controller 20 finely controls the conveyor motor 12a with inverter control so that the conveying speed of the conveyor unit 12 matches a set speed inputted by an operator to the touch panel display 30. The encoder 12b detects the speed of the conveyor motor 12a and transmits the detection results to the controller 20.

(2-3) X-ray Emitter

The X-ray emitter 13 is an example of an X-ray source. The X-ray emitter 13 emits X-rays toward an article P conveyed by the conveyor unit 12. The X-ray emitter 13 is disposed above the conveyor unit 12, as shown in FIG. 3. The X-ray emitter 13 emits X-rays in a fan-shaped emission range Y toward the first line sensor 14 and the second line sensor 15 disposed below the conveyor unit 12. The emission range Y of the X-ray emitter 13 extends vertically with respect to the conveying surface of the conveyor unit 12, as shown in FIG. 3. Also, the emission range Y widens in the direction orthogonal to the conveying direction D of the conveyor unit 12 (width direction of the belt 12d).

(2-4) Line Sensors

The first line sensor 14 and the second line sensor 15 detect X-rays emitted from the X-ray emitter 13 and transmitted through the article P and the belt 12*d*. The first line sensor 14 and the second line sensor 15 are sensors for detecting X-rays in mutually different energy bands (wavelength). The first line sensor 14 detects X-rays in a low-energy band (relatively long wavelength). The second line sensor 15 detects X-rays in a high-energy band (relatively short wavelength), which is different from the energy band detected by the first line sensor 14.

The first line sensor 14 and the second line sensor 15 are vertically arranged, as shown in FIG. 3. The second line sensor 15 is disposed below the first line sensor 14. Among the X-rays emitted by the X-ray emitter 13, those in the low-energy band are detected by the first line sensor 14. Among the X-rays that have passed through the first line sensor 14, those in a middle energy band (X-rays in an energy band between the above-noted high energy band and low energy band) are removed by a filter (not shown) disposed between the first line sensor 14 and the second line sensor 15. X-rays in the high energy band transmitted through the filter are detected by the second line sensor 15.

The first line sensor 14 mainly includes numerous X-ray detection elements 14*a* (see 3). The second line sensor 15 mainly includes numerous X-ray detection elements 15*a* (see FIG. 3). The first line sensor 14 and second line sensor 15 are installed in a designed predetermined position, whereby the X-ray detection elements 14*a*, 15*a* are designed so as to be installed horizontally on a straight line in an orientation orthogonal to the conveying direction D of the conveyor unit 12.

However, the first line sensor 14 and the second line sensor 15 may be installed in a position displaced in the horizontal direction and/or the vertical direction from a predetermined position in assembly. As a result, the orientation in which the X-ray detection elements 14*a*, 15*a* line up may not be horizontal or may be tilted from the orientation orthogonal to the conveying direction D of the conveyor unit 12. Also, the X-ray detection elements 14*a*, 15*a* may be displaced in the conveying direction D of the article P, the direction orthogonal to the conveying direction D, or the vertical direction (up-down direction) as a result of the first line sensor 14 and the second line sensor 15 being installed so as to be displaced from a predetermined position originally intended for installation, even when the X-ray detection elements 14*a*, 15*a* are lined up in an orientation orthogonal to the conveying direction D and horizontally on a straight line.

The first and second line sensors 14, 15 detect the amount of X-rays (amount of transmitted X-rays) that have passed through the article P and the belt 12*d* for X-rays in the energy bands to be detected thereby, respectively, and output X-ray transmission signals that are based on the amount of transmitted X-rays. In other words, the first and second line sensors 14, 15 output X-ray transmission signals that correspond to the intensity of the transmitted X-rays. The intensity of the transmitted X-rays depends on the amount of transmitted X-rays. The brightness (luminance) of the image generated by a first X-ray image generation unit 22*a* of the later-described controller 20 is determined based on the X-ray transmission signals outputted by the first line sensor 14. The brightness (luminance) of the image generated by a second X-ray image generation unit 22*b* of the later-described controller 20 is determined based on the X-ray transmission signals outputted by the second line sensor 15.

FIG. 4 is a graph showing an example of the amount of transmitted X-rays (detection amount) detected by the X-ray detection elements 14*a* of the first line sensor 14 and X-ray detection elements 15*a* of the second line sensor 15. Having two line sensors 14, 15 for different X-ray energy bands to be detected makes it possible to obtain a graph (solid line G1) of the detection results of the first line sensor 14 and a graph (broken line G2) of the detection results of the second line sensor 15 (FIG. 4). The horizontal axis of the graph of FIG. 4 corresponds to the positions of the X-ray detection elements 14*a*, 15*a*. In other words, the horizontal axis of the graph corresponds to the distance in the direction orthogonal to the conveying direction D of the conveyor unit 12 (width direction of the belt 12*d*). The vertical axis of the graph indicates the amount of transmitted X-rays (detection amount) detected by the X-ray detection elements 14*a*, 15*a*.

In the transmitted images (first X-ray image and second X-ray image) generated by the first X-ray image generation unit 22*a* and the second X-ray image generation unit 22*b*, the locations having a high amount of transmitted X-rays appear bright, and the locations having a low amount of transmitted X-rays appear dark. In other words, the lightness and darkness (luminance) of the transmitted images generated by the first X-ray image generation unit 22*a* and the second X-ray image generation unit 22*b* correspond to the amount of transmitted X-rays.

Here, the first line sensor 14 also functions as a sensor for detecting the timing at which the article P passes through the emission range Y of the X-rays (see FIG. 3). Specifically, when the article P conveyed by the conveyor unit 12 has arrived at the position (emission range Y) above the first line sensor 14, any of the X-ray detection elements 14*a* of the first line sensor 14 outputs an X-ray transmission signal (first signal) indicating a voltage that is equal to or less than a predetermined threshold value. Also, when the article P has finished passing through the emission range Y, all of the X-ray detection elements 14*a* of the first line sensor 14 output an X-ray transmission signal (second signal) indicating voltage above the predetermined threshold value. The first and second signals are inputted to the later-described controller 20, whereby the presence of an article P in the emission range Y is detected.

(2-5) Touch Panel Display

The touch panel display 30 is a liquid crystal display having a touch panel function. The touch panel display 30 is electrically connected to the controller 20 and exchanges signals with the controller 20.

The touch panel display 30 functions as a display unit and an input unit. For example, the touch panel display 30 displays the X-ray image, the results of inspection for foreign matter, etc. Also, the touch panel display 30 receives a variety of settings and information inputted by the operator.

(2-6) Controller

The controller 20 controls the operation of each part of the X-ray inspection device 10. The controller 20 carries out foreign matter inspection based on the detection results of the amount of transmitted X-rays by the first and second line sensors 14, 15.

The controller 20 mainly includes a central processing unit (CPU), read-only memory (ROM), random access memory (RAM), a hard disk drive (HDD), and the like.

The controller 20 has a storage unit 21 and a control unit 22, as shown in FIG. 5. The controller 20 also has a display control circuit, a key input circuit, a communication port, and the like (not shown). The display control circuit controls the data display of the touch panel display 30. The key input circuit takes in key input data inputted by the operator via the touch panel of the touch panel display 30. The communication port can be connected to a printer, the sorting mechanism 70 or other external device, or a LAN or other network.

The controller 20 is electrically connected to the conveyor motor 12*a*, the encoder 12*b*, the X-ray emitter 13, the first line sensor 14, the second line sensor 15, and the touch panel display 30 (see FIG. 5). The controller 20 acquires data related to the speed of the conveyor motor 12*a* from the encoder 12*b*, and ascertains the movement distance and movement speed of the article P based on these data.

(2-6-1) Storage Unit

The storage unit 21 mainly includes a ROM, RAM, HDD, and the like, and stores various programs to be executed by the control unit 22, various settings for controlling each part of the X-ray inspection device 10, and various information. The storage unit 21 includes a luminance-adjustment-formula storage area 21*a* and a correction parameter storage area 21*b*, as shown in FIG. 5.

(2-6-1-1) the Luminance-Adjustment-Formula Storage Area

The luminance-adjustment-formula storage area 21*a* stores a luminance adjustment formula. The luminance adjustment formula is information used by a determination unit 22*e* of the later-described control unit 22 to adjust the luminance of the pixels of the later-described second X-ray images or corrected second X-ray images. The luminance adjustment formula is created so that there is a match between the luminance of pixels of a later-described first X-ray image and a later-described corrected second X-ray image (or second X-ray image) after an adjustment for luminance, for the pixels being obtained based on the X-rays that have passed through the same location of the article P, in a case when X-rays that have passed through an article P having no foreign matter are detected by the first line sensor 14 and the second line sensor 15, and the first X-ray image and the corrected second X-ray image (or the second X-ray image) are generated based on the detection results, and the corrected second X-ray image (or the second X-ray image) is adjusted for luminance using the luminance adjustment formula. The luminance adjustment formulas are stored in advance in the luminance-adjustment-formula storage area 21*a* e.g., for each type of article P. However, no limitation is imposed thereby; for example, the luminance adjustment formula may be inputted from the touch panel display 30. For example, the luminance adjustment formula may be generated by the control unit 22 by obtaining the first X-ray image and the corrected second X-ray image (or second X-ray image) for articles P known to be devoid of foreign matter during test operation or the like.

(2-6-1-2) Correction Parameter Storage Area

The correction parameter storage area 21*b* stores a corrected parameter calculated by a calculation unit 22*cb* of a later-described correction parameter generation unit 22*c*. The corrected parameter is used by a later-described corrected-image generation unit 22*d* to generate a corrected second X-ray image by correcting a second X-ray image of the article P obtained based on the detection results of the second line sensor 15.

(2-6-2) Control Unit

The control unit 22 mainly includes a CPU, and executes programs stored in the storage unit 21 to thereby control the operation of each part of the X-ray inspection device 10. The control unit 22 also executes programs stored in the storage unit 21 to thereby carry out foreign matter inspection based on the detection results of the amount of transmitted X-rays by the first line sensor 14 and second line sensor 15.

The control unit 22 mainly has the first X-ray image generation unit 22*a*, the second X-ray image generation unit 22*b*, the correction parameter generation unit 22*c*, the corrected-image generation unit 22*d*, and a determination unit 22*e* as function units (FIG. 5).

(2-6-2-1) First X-ray Image Generation Unit

The first X-ray image generation unit 22*a* generates a first X-ray image (a low-energy X-ray image) as a transmission image based on the amount of transmitted X-rays of the X-rays in a low-energy band detected by the first line sensor 14.

Specifically, the first X-ray image generation unit 22*a* acquires, in short time intervals, X-ray transmission signals that correspond to the intensity of X-rays that have passed through the article P or the like being outputted from the respective X-ray detection elements 14*a* of the first line sensor 14, and generates the first X-ray image based on the acquired X-ray transmission signals. In particular, the first X-ray image generation unit 22*a* generates the first X-ray image based on the X-ray transmission signals outputted from the respective X-ray detection elements 14*a* when the article P passes through the emission range Y of X-rays (see FIG. 3). The first X-ray image generation unit 22*a* chronologically connects together the short-time-interval data related to the intensity of the X-rays obtained from the respective X-ray detection elements 14*a* in the form of a matrix. The presence of an article P in the X-ray emission range Y is determined by a signal outputted by the first line sensor 14 as described above.

In the first X-ray image generated by the first X-ray image generation unit 22*a*, locations where a high amount of transmitted X-rays is detected by the X-ray detection elements 14*a* appear bright (pale, high luminance), and the locations where a low amount of transmitted X-rays is detected by the X-ray detection elements 14*a* appear dark (deep, low luminance). The first X-ray image has, e.g., 256 gradations.

(2-6-2-2) Second X-ray Image Generation Unit

The second X-ray image generation unit 22*b* generates a second X-ray image (a high-energy X-ray image) as a transmission image based on the amount of transmitted X-rays of the X-rays in a high-energy band detected by the second line sensor 15.

The second X-ray image generation unit 22*b* is different from the first X-ray image generation unit 22*a* in terms of generating an X-ray image based on the X-ray transmission signals outputted from the respective X-ray detection elements 15*a* of the second line sensor 15.

The second X-ray image generation unit 22*b* is different from the first X-ray image generation unit 22*a* in terms that the second X-ray image generation unit 22*b* generates a second X-ray image by making an X-ray image based on the X-ray transmission signals outputted from the X-ray detection elements 15*a* and then reducing the X-ray image by a predetermined factor. The second X-ray image generation unit 22*b* carries out such processing for the following reasons.

A process for obtaining a differential image between the first X-ray image and the second X-ray image (including the corrected second X-ray image obtained by correcting the second X-ray image) is carried out in the later-described determination unit 22*e*. Accordingly, the sizes of the first X-ray image and the second X-ray image are preferably harmonized. The second line sensor 15 is installed below the first line sensor 14 in the X-ray inspection device 10. Also, X-rays are emitted from the X-ray emitter 13 in a fan-shaped emission range Y in the X-ray inspection device 10. For this reason, an X-ray image obtained using the detection results of the second line sensor 15, which detects X-rays below the first line sensor 14, becomes larger than the first X-ray image. Therefore, the second X-ray image generation unit 22b carries out a process in which the X-ray image generated based on the X-ray transmission signals outputted from the X-ray detection elements 15a is reduced by the predetermined factor calculated based on the designed predetermined mounting positions for the first line sensor 14 and the second line sensor 15.

The process executed by the second X-ray image generation unit 22b to reduce the X-ray image by the predetermined factor is carried out on the premise that the first line sensor 14 and the second line sensor 15 are disposed in the predetermined designed position. Correction of the second X-ray image (generation of the corrected second X-ray image), which is carried out as a countermeasure for when the line sensors 14, 15 are mounted displaced from predetermined positions, is described later.

(2-6-2-3) Correction Parameter Generation Unit

The correction parameter generation unit 22c detects positional displacement of the second line sensor 15 with respect to the first line sensor 14 in horizontal and vertical direction and generates a correction parameter to be used by the corrected-image generation unit 22d to generate a corrected second X-ray image in accordance with the positional displacement of the second line sensor 15. The corrected second X-ray image is an image obtained by performing a correction process to the second X-ray image so that the pixels of the first X-ray image based on the X-rays that have passed through a certain portion of the article P are superimposed on the pixels of the X-ray image based on the X-rays that have passed through the same portion of the article P in order for the later-described determination unit 22e to execute difference processing between the first X-ray image and the second X-ray image.

The correction parameter generation unit 22c has a detection unit 22ca and a calculation unit 22cb as sub-function units.

The detection unit 22ca detects positional displacement of the second line sensor 15 with respect to the first line sensor 14 in horizontal and vertical direction.

The calculation unit 22cb calculates the correction parameter to be used by the corrected-image generation unit 22d to generate the corrected second X-ray image when positional displacement of the second line sensor 15 with respect to the first line sensor 14 is detected by the detection unit 22ca.

The process executed by the detection unit 22ca and the calculation unit 22cb is later described.

(2-6-2-4) Corrected-image Generation Unit

The corrected-image generation unit 22d generates, based on the detection results of the detection unit 22ca, a corrected second X-ray image by correcting the second X-ray image of an article P obtained based on the detection results of the second line sensor 15. Specifically, when the detection unit 22ca detects positional displacement of the second line sensor 15 with respect to the first line sensor 14, the corrected-image generation unit 22d generates the corrected second X-ray image, which is obtained by correcting the second X-ray image of the article P, using a correction parameter stored in the correction parameter storage area 21b.

The process for generating the corrected second X-ray image by the corrected-image generation unit 22d is later described.

(2-6-2-5) Determination Unit

The determination unit 22e determines whether an article P is contaminated with foreign matter based on the first X-ray image generated by the first X-ray image generation unit 22a, and the second X-ray image generated by the second X-ray image generation unit 22b or the corrected second X-ray image generated by the corrected-image generation unit 22d.

Specifically, the determination unit 22e determines whether an article P is contaminated with foreign matter in the following manner.

The determination unit 22e carries out a process in the following manner using the second X-ray image when a corrected second X-ray image is not generated, and using the corrected second X-ray image when the corrected second X-ray image is generated. An example in which the determination unit 22e uses the corrected second X-ray image is explained below. When the determination unit 22e uses the second X-ray image, the corrected second X-ray image described below can be read as the second X-ray image.

First, the determination unit 22e carries out a process to adjust the luminance of the corrected second X-ray image using the luminance adjustment formula stored in the luminance-adjustment-formula storage area 21a. Next, the determination unit 22e generates a differential image based on the difference in luminance of respective pixels in the first X-ray image and the luminance-adjusted corrected second X-ray image. As described above, the luminance adjustment formula is determined so that there is a match between the luminance of the pixel of the first X-ray image and the luminance of the pixel of the luminance-adjusted corrected second X-ray image which are obtained based on the X-rays that have passed through the same location of the article P in a case when the first X-ray image and the corrected second X-ray image are generated based on the X-rays that have passed through an article P that is not contaminated with foreign matter and the luminance of the corrected second X-ray image is adjusted using the luminance adjustment formula. For this reason, if the article P is not contaminated with foreign matter, the value of each of the pixels of the first X-ray image and the value of the corresponding pixel of the luminance-adjusted corrected second X-ray image substantially match each other. On the other hand, when the article P is contaminated with foreign matter, there will be a difference between the value of each of the pixels of the first X-ray image and the value of the corresponding pixel of the luminance-adjusted corrected second X-ray image due to the difference in characteristics between the foreign matter and the article P. Using this principle, the determination unit 22e determines whether the article P is contaminated or not with foreign matter based on the differential image. The determination results (results of foreign matter inspection) produced by the determination unit 22e are outputted to the touch panel display 30. The determination results produced by the determination unit 22e are also transmitted to the sorting mechanism 70.

(3) Process Executed by the Controller

The process executed by the controller 20 will be described particularly in relation to the process carried out by the correction parameter generation unit 22c and the process carried out by the corrected-image generation unit 22d.

(3-1) Process Carried Out by the Correction Parameter Generation Unit

The process carried out by the correction parameter generation unit 22c will be described.

The process carried out by the correction parameter generation unit 22c is executed at the time of, e.g., installation or test operation of the X-ray inspection device 10, and the correction parameter generation unit 22c detects, in advance, positional displacement of the second line sensor 15 with respect to the first line sensor 14. The correction parameter generation unit 22c executes the process when a command for generating the correction parameter (a command for detecting positional displacement of the second line sensor 15 with respect to the first line sensor 14) is inputted to the touch panel display 30 by an operator, for example, in the installation of the X-ray inspection device 10.

When the correction parameter is to be calculated, a sample S is conveyed by the conveyor unit 12 in place of the article P. The sample S has a known shape. For example, the sample S is formed in a rectangular shape as viewed from above and is a flat sheet of fixed thickness (see FIG. 6). X-rays are emitted from the X-ray emitter 13 to the sample S conveyed by the conveyor unit 12. The correction parameter generation unit 22c detects positional displacement of the second line sensor 15 with respect to the first line sensor 14 based on the detection result of the first line sensor 14 and the second line sensor 15 of X-rays that have passed through the sample S. More specifically, the correction parameter generation unit 22c detects displacement of the second line sensor 15 with respect to the first line sensor 14 based on the first X-ray image generated on the basis of the amount of transmitted X-rays in a low-energy band detected by the first line sensor 14 and the second X-ray image generated on the basis of the amount of transmitted X-rays in a high-energy band detected by the second line sensor 15. The correction parameter generation unit 22c generates a correction parameter to be used by the corrected-image generation unit 22d to generate a corrected second X-ray image in accordance with positional displacement when positional displacement of the second line sensor 15 with respect to the first line sensor 14 is detected.

It will be explained in detail below how the detection unit 22ca and the calculation unit 22cb of the correction parameter generation unit 22c carry out the process.

In the following explanation, a first image C1 and a second image C2 (see FIGS. 7 to 12) are used in the detection of positional displacement of the second line sensor 15 with respect to the first line sensor 14 and in the generation of a correction parameter. The first image C1 is an image binarized using a predetermined threshold value so that the first X-ray image of the sample S is broken down into pixels representing the sample S and pixels representing a background portion. The area in which the pixels representing the sample S are present in the first image C1 shall be referred to as first area A1 (see FIGS. 7 to 12). The second image C2 is an image binarized using a predetermined threshold value so that the second X-ray image of the sample S is broken down into pixels representing the sample S and pixels representing a background portion. The area in which the pixels representing the sample S are present in the second image C2 shall be referred to as second area A2 (see FIGS. 7 to 12).

FIGS. 7 to 12 are examples of drawings depicting the first image C1 and the second image C2 created for the sample S in a superimposing manner. In FIGS. 7 to 12, the first image C1 and the second image C2 are disposed so that the first area A1 and the second area A2 exactly overlaps each other when there is no positional displacement of the second line sensor 15 with respect to the first line sensor 14. In FIGS. 7 to 12, the two-dot-chain line represents the edges of the first image C1 and the second image C2, the area surrounded by a solid line represents the first area A1, and the area surrounded by a broken line represents the second area A2.

The direction D' in FIGS. 7 to 12 corresponds to the direction in which the sample S is conveyed (conveying direction D of the conveyor unit 12). Below, to describe the direction in the first image C1 and the second image C2, the direction for which the direction D' heads shall be referred to as forward, the direction which opposes the direction D' shall be referred to as rearward, the right side when facing the direction D' shall be referred to as rightward, and the left side when facing the direction D' shall be referred to as leftward (see FIGS. 7 to 12).

As an example, a case in which the first line sensor 14 is installed in a predetermined designed position will be explained here. Also, here, a case in which a rectangular sample S is placed on the belt 12d in an orientation in which the long sides extend along the conveying direction D of the conveyor unit 12 will be explained as an example. However, no limitation is imposed thereby; the sample S may be placed on the belt 12d in any orientation.

The detection unit 22ca detects positional displacement of the second line sensor with respect to the first line sensor 14 in the horizontal and vertical directions regarding the following six patterns (a) to (f). The calculation unit 22cb calculates the correction parameter when the detection unit 22ca detects positional displacement of the second line sensor 15.

(a) Positional Displacement in the Vertical Direction

Figure 13A:
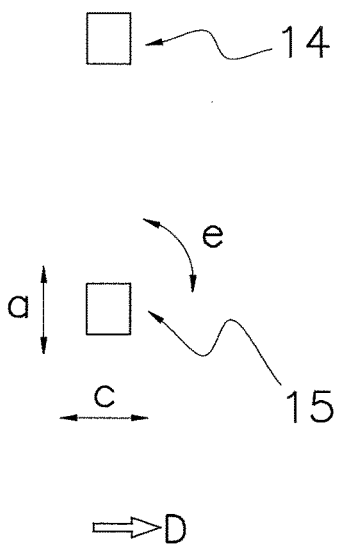
FIG. 13A is a drawing illustrating the displacement direction of the second line sensor with respect to the first line sensor, and is a view of the first and second line sensors as viewed from the side, the arrow D in the drawing indicating the conveying direction of the conveyor unit.

Detection of positional displacement (displacement in the direction of arrow a in FIG. 13A) of the second line sensor 15 with respect to the first line sensor 14 in the vertical direction (up-down direction) by the detection unit 22ca, and calculation of the correction parameter by the calculation unit 22cb when such a positional displacement of the second line sensor 15 is detected will be described in reference to FIG. 7.

The detection unit 22ca detects that the second line sensor 15 is displaced with respect to the first line sensor 14 in the vertical direction when the sizes of the first area A1 and the second area A2 are different. Specifically, the detection unit 22ca detects that the second line sensor 15 is displaced with respect to the first line sensor 14 in the vertical direction when the value of the ratio of the length L21 of the left end of the second area A2 with respect to the length L11 of the left end of the first area A1 and the value of the ratio of the length L22 of the back end of the second area A2 with respect to the length L12 of the back end of the first area A1 (see FIG. 7) are the same value but not 1. Here, the end parts of the first area A1 and the second area A2 are ascertained by, e.g., executing an edge detection processing to the first area A1 and the second area A2.

The calculation unit 22cb calculates as a scaling factor K an amount by which the second area A2 should be enlarged or reduced to match the size of the first area A1 when the detection unit 22ca has detected positional displacement of the second line sensor 15 with respect to the first line sensor 14 in the vertical direction. Specifically, the calculation unit 22cb calculates a value obtained by dividing the above-noted L11 by L21 as the scaling factor K (see FIG. 7). The calculated scaling factor K is stored in the correction parameter storage area 21b as a correction parameter.

(b) Horizontal-direction Tilt

Detection of horizontal-direction tilt (rotational positional displacement in horizontal direction) of the second line sensor 15 with respect to the first line sensor 14 by the detection unit 22*ca*, and calculation of the correction parameter by the calculation unit 22*cb* when such a positional displacement of the second line sensor 15 is detected will be described in reference to FIG. 8. Horizontal-direction tilt of the second line sensor 15 with respect to the first line sensor 14 means rotational displacement in the direction of arrow b in FIG. 13C.

The detection unit 22*ca* detects horizontal-direction tilt of the second line sensor 15 with respect to the first line sensor 14 based on the tilt of the second area A2 with respect to first area A1. Specifically, the detection unit 22*ca* detects horizontal-direction tilt of the second line sensor 15 with respect to the first line sensor 14 based on the tilt of the line H21 of the left end of the second area A2 with respect to the line H11 of the left end of the first area A1. In this example, the line H11 of the left end of the first area A1 extends parallel to the direction D' as shown in FIG. 8. The detection unit 22*ca* therefore determines whether the line H21 of the left end of the second area A2 is parallel to the direction D', and, when the line H21 and the direction D' are not parallel, detects the horizontal-direction tilt of the second line sensor 15 with respect to the first line sensor 14.

The calculation unit 22*cb* calculates an angle of the tilt of the second area A2 with respect to the first area A1 when the detection unit 22*ca* has detected the horizontal-direction tilt of the second line sensor 15 with respect to the first line sensor 14. Specifically, the calculation unit 22*cb* calculates, for example, an angle θ of the line H21 of the left end of the second area A2 with respect to the direction D', as the correction parameter (see FIG. 8). In this example, the angle θ is expressed as a positive value when the line H21 of the left end of the second area A2 is tilted in the counterclockwise direction with respect to the direction D', and the angle θ is expressed as a negative value when the line H21 of the left end of the second area A2 is tilted in the clockwise direction with respect to the direction D'. The calculated angle θ is stored in the correction parameter storage area 21*b* as a correction parameter.

(c) Positional Displacement in the Conveying Direction

Detection of positional displacement of the second line sensor 15 with respect to the first line sensor 14 to the upstream side or the downstream side of the conveying direction D (displacement in the direction of arrow c in FIG. 13A) by the detection unit 22*ca*, and calculation of the correction parameter by the calculation unit 22*cb* when such a positional displacement of the second line sensor 15 is detected will be described in reference to FIG. 9.

The detection unit 22*ca* detects the positional displacement of the second line sensor 15 with respect to the first line sensor 14 to the upstream side or downstream side in the conveying direction D based on the displacement of the second area A2 with respect to the first area A1 in the front-back direction. Specifically, the detection unit 22*ca* detects the positional displacement of the second line sensor 15 with respect to the first line sensor 14 to the upstream side or downstream side of the conveying direction D when the position of the line H22 of the back end of the second area A2 does not match the position of the line H12 of the back end of the first area A1 (see FIG. 9).

The calculation unit 22*cb* calculates a magnitude of the positional displacement of the second area A2 with respect to the first area A1 when the detection unit 22*ca* has detected positional displacement of the second line sensor 15 with respect to the first line sensor 14 to the upstream side or the downstream side of the conveying direction D. Specifically, the calculation unit 22*cb* calculates, e.g., the distance B1 between the position of the line H12 of the back end of the first area A1 and the position of the line H22 of the back end of the second area A2 (see FIG. 9). The calculation unit 22*cb* expresses the value of the distance B1 as a positive value when the line H22 of the back end of the second area A2 is displaced forward with respect to the line H12 of the back end of the first area A1, and expresses the value of the distance B1 as a negative value when the line H22 is displaced rearward with respect to the line H12. The calculated distance B1 is stored in the correction parameter storage area 21*b* as a correction parameter.

Figure 13B:
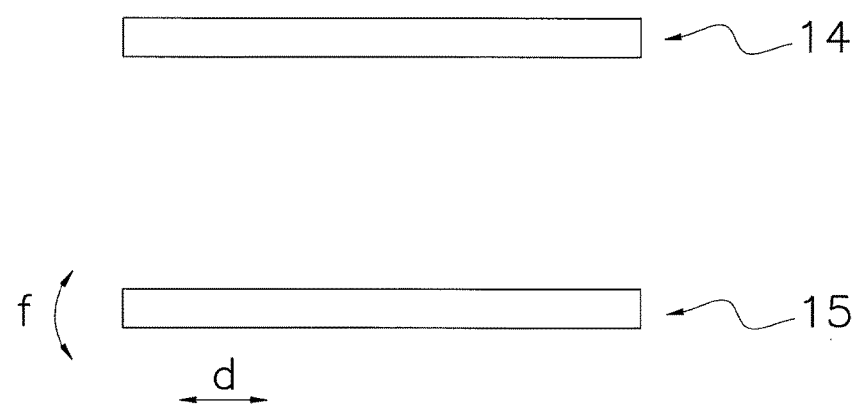
FIG. 13B is a drawing illustrating the displacement direction of the second line sensor with respect to the first line sensor, and is a view of the first and second line sensors as viewed from the downstream side in the conveying direction.

(d) Positional Displacement in the Direction Orthogonal to the Conveying Direction Detection of positional displacement of the second line sensor 15 with respect to the first line sensor 14 in the direction orthogonal to the conveying direction D as viewed from above (displacement in the direction of arrow d in FIG. 13B) by the detection unit 22*ca*, and calculation of the correction parameter by the calculation unit 22*cb* when such a positional displacement of the second line sensor 15 is detected will be described in reference to FIG. 10.

The detection unit 22*ca* detects displacement of the second line sensor 15 with respect to the first line sensor 14 in the direction orthogonal to the conveying direction D as viewed from above based on the displacement of the second area A2 with respect to the first area A1 in the right-left direction. Specifically, the detection unit 22*ca* detects positional displacement of the second line sensor 15 with respect to the first line sensor 14 in the direction orthogonal to the conveying direction D as viewed from above when the position of the line H11 of the left end of the first area A1 and the position of the line H21 at the left end of the second area A2 do not match each other (see FIG. 10).

The calculation unit 22*cb* calculates a magnitude of the positional displacement of the second area A2 with respect to the first area A1 when the detection unit 22*ca* has detected positional displacement of the second line sensor 15 with respect to the first line sensor 14 in the direction orthogonal to the conveying direction D. Specifically, the calculation unit 22*cb* calculates, e.g., the distance B2 between the position of the line H11 of the left end of the first area A1 and the position of the line H21 of the left end of the second area A2. The calculation unit 22*cb* expresses the value of the distance B2 as a positive value when the line H21 of the left end of the second area A2 is displaced leftward with respect to the line H11 of the left end of the first area A1, and expresses the value of the distance B2 as a negative value when the line H21 is displaced rightward with respect to the line H11. The calculated distance B2 is stored in the correction parameter storage area 21*b* as a correction parameter.

(e) Vertical-direction Tilt Along the Conveying Direction

Detection of vertical-direction tilt (rotational positional displacement in vertical direction) of the second line sensor 15 with respect to the first line sensor 14 along the conveying direction D by the detection unit 22*ca*, and calculation of the correction parameter by the calculation unit 22*cb* when such a positional displacement of the second line sensor 15 is detected will be described with reference to FIG. 11. Vertical-direction tilt of the second line sensor 15 with respect to the first line sensor 14 along the conveying direction D means rotational displacement in the direction of arrow e in FIG. 13A.

The detection unit 22*ca* detects vertical-direction tilt of the second line sensor 15 with respect to the first line sensor 14 along the conveying direction D based on the enlargement/reduction of the second area A2 with respect to the first area A1 in the direction D'. Specifically, the detection unit 22ca detects vertical-direction tilt of the second line sensor 15 along the conveying direction D with respect to the first line sensor 14 when the value of the ratio of the length L21 of the left end of the second area A2 with respect to the length L11 of the left end of the first area A1 and the value of the ratio of the length L22 of the back end of the second area A2 with respect to the length L12 of the back end of the first area A1 are not the same (see FIG. 11).

The calculation unit 22cb determines a scaling factor M in the front-back direction of the second image C2 when the detection unit 22ca has detected the vertical-direction tilt of the second line sensor 15 with respect to the first line sensor 14 along the conveying direction D. Specifically, the calculation unit 22cb calculates a value of the ratio (L11/L21) of the length L11 of the left end of the first area A1 and the length L21 of the left end of the second area A2 (see FIG. 11) as the scaling factor M. The calculated scaling factor M is stored in the correction parameter storage area 21b as a correction parameter.

(f) Vertical-direction Tilt Along the Direction Orthogonal to the Conveying Direction Detection of vertical-direction tilt (rotational positional displacement in vertical direction) of the second line sensor 15 with respect to the first line sensor 14 along the direction orthogonal to the conveying direction D by the detection unit 22ca, and calculation of the correction parameter by the calculation unit 22cb when such a positional displacement of the second line sensor 15 is detected will be described with reference to FIG. 12. Vertical-direction tilt of the second line sensor 15 with respect to the first line sensor 14 along the direction orthogonal to the conveying direction D means rotational displacement in the direction of arrow f in FIG. 13B.

The detection unit 22ca detects vertical-direction tilt of the second line sensor 15 with respect to the first line sensor 14 along the direction orthogonal to conveying direction D based on the state of enlargement/reduction of the second area A2 with respect to first area A1 along the direction orthogonal to the direction D'. Specifically, the detection unit 22ca compares the value of the ratio of the length L11 of the left end of the first area A1 with respect to the length L21 of the left end of the second area A2 and the value of the ratio of the length L13 of the right end of the first area A1 with respect to the length L23 of the right end of the second area A2, and when these values are not the same, the detection unit 22ca detects vertical-direction tilt of the second line sensor 15 with respect to the first line sensor 14 along the direction orthogonal to the conveying direction D (see FIG. 12).

The calculation unit 22cb determines a scaling factor N1 of the left end of the second image C2 in the front-back direction and a scaling factor N2 of the right end of the second image C2 in the front-back direction when the detection unit 22ca has detected vertical-direction tilt of the second line sensor 15 with respect to the first line sensor 14 along the direction orthogonal to the conveying direction D. The calculation unit 22cb first calculates the value of the ratio of the length L11 of the left end of the first area A1 with respect to the length L21 of the left end of the second area A2 (=L11/L21) and the value of the ratio of the length L13 of the right end of the first area A1 with respect to the length L23 of the right end of the second area A2 (=L13/L23) (FIG. 12). Based on these values of the ratio and information regarding the positions of the left and right ends of the second area A2 in the second image C2, the calculation unit 22cb calculates the scaling factor N1 of the left end of the second image C2 and the scaling factor N2 of the right end of the second image C2, so that the value of L11/L21 and the value of L13/L23 match. In other words, the calculation unit 22cb calculates the scaling factors N1, N2 so that the two values of the ratio (L11/L21 and L13/L23) match in a case partial scaling factors of the second image C2 in the front-back direction are determined so as to continuously change from the scaling factor N1 to the scaling factor N2 from the left end to the right end along the right-left direction, and when these partial scaling factors are to be applied. The scaling factor N1 and scaling factor N2 are determined so that the center portion of the second image C2 in the right-left direction is neither enlarged nor reduced. The calculation unit 22cb also determines a scaling factor N3 of the second image C2 in the right-left direction when the detection unit 22ca has detected vertical-direction tilt of the second line sensor 15 with respect to the first line sensor 14 along the direction orthogonal to the conveying direction D. Specifically, the calculation unit 22cb calculates as the scaling factor N3 (=L15/L25) a value of the ratio of the distance L15 between the line H11 of the left end and the line H13 of the right end of the first area A1 with respect to the distance L25 between the line H21 of the left end and the line H23 of the right end of the second area A2 (see FIG. 11). The calculated scaling factor N1, scaling factor N2, and scaling factor N3 are stored in the correction parameter storage area 21b as correction parameters.

(3-2) Process for Generating the Corrected Second X-ray Image

The process with which corrected-image generation unit 22d generates the corrected second X-ray image is described below. Here, the directions shown in FIG. 14 will be used in the following description. In the second X-ray image E shown in FIG. 14, the direction D" corresponds to the direction in which the article P is conveyed (conveying direction D of the conveyor unit 12). The directions in the second X-ray image E shall be referred to below as follows: the direction for which the direction D" heads shall be referred to as forward, the direction opposing the direction D" shall be referred to as rearward, the right side when facing the direction D" shall be referred to as rightward, and the left side when facing the direction D" shall be referred to as leftward (see FIG. 14).

The corrected-image generation unit 22d generates the corrected second X-ray image, in which the second X-ray image E of the article P has been corrected, based on the detection results of the detection unit 22ca of the correction parameter generation unit 22c. Specifically, when the detection unit 22ca detects positional displacement of the second line sensor 15 with respect to the first line sensor 14 and the correction parameter has been calculated by the calculation unit 22cb, the corrected-image generation unit 22d generates the corrected second X-ray image by correcting the second X-ray image E of the article P using the calculated correction parameter (stored in the correction parameter storage area 21b).

More specifically, the corrected-image generation unit 22d generates the corrected second X-ray image as in (a) to (f) below using the correction parameters stored in the correction parameter storage area 21b.

(a) When Positional Displacement in the Vertical Direction has been Detected

The corrected-image generation unit 22d generates the corrected second X-ray image by enlarging or reducing the second X-ray image E using the scaling factor K stored in the correction parameter storage area 21*b*.

(b) When Horizontal-direction Tilt has been Detected

The corrected-image generation unit 22*d* generates the corrected second X-ray image by rotating the second X-ray image E in the clockwise direction by an angle θ (by rotation in the counter-clockwise direction when the angle θ is a negative value) stored in the correction parameter storage area 21*b*.

(c) When Positional Displacement to the Upstream Side or Downstream Side in the Conveying Direction has been Detected The corrected-image generation unit 22*d* generates the corrected second X-ray image by moving the second X-ray image E rearward by a distance B1 stored in the correction parameter storage area 21*b* (and by moving the second X-ray image forward when the distance B1 is a negative value) (see FIG. 14). In other words, the corrected-image generation unit 22*d* generates the corrected second X-ray image by moving the second X-ray image E to the upstream side or downstream side in the direction D″, which corresponds to the upstream side or downstream side in the conveying direction D, by the distance B1 stored in the correction parameter storage area 21*b* (see FIG. 14).

(d) When Positional Displacement in the Direction Orthogonal to the Conveying Direction has been Detected The corrected-image generation unit 22*d* generates the corrected second X-ray image by moving the second X-ray image E rightward by a distance B2 stored in the correction parameter storage area 21*b* (and leftward when the distance B2 is a negative value) (see FIG. 14). In other words, the corrected-image generation unit 22*d* generates the corrected second X-ray image by moving the second X-ray image E in the direction orthogonal to the direction D″, which corresponds to the direction orthogonal to the conveying direction D, by the distance B2 stored in the correction parameter storage area 21*b* (see FIG. 14).

(e) When Vertical-direction Tilt Along the Conveying Direction has been Detected The corrected-image generation unit 22*d* generates the corrected second X-ray image by enlarging/reducing the second X-ray image E by a scaling factor M in the front-back direction based on the scaling factor M stored in the correction parameter storage area 21*b*. In other words, the corrected-image generation unit 22*d* generates the corrected second X-ray image by enlarging or reducing the second X-ray image E in the direction D″, which corresponds to the tilt direction (conveying direction D) of the second line sensor 15 (see FIG. 14).

(f) The Case in which Vertical-direction Tilt Along the Direction Orthogonal to the Conveying Direction has been Detected The corrected-image generation unit 22*d* enlarges/reduces the left end of the second X-ray image E by the scaling factor N1 in the front back direction and reduces/enlarges the right end of the second X-ray image E in the front back direction by the scaling factor N2 based on the scaling factor N1 and scaling factor N2 stored in the correction parameter storage area 21*b*. The corrected-image generation unit 22*d* enlarges/reduces the intermediate portions of the second X-ray image between the left and right ends with a scaling factor determined so as to continuously change from the scaling factor N1 to the scaling factor N2 from the left end to the right end of the second X-ray image. The corrected-image generation unit 22*d* generates the corrected second X-ray image by further enlarging/reducing the second X-ray image, which is enlarged/reduced in the front back direction, in right and left direction by the scaling factor N3 based on the scaling factor N3 stored in the correction parameter storage area 21*b*. In other words, the corrected-image generation unit 22*d* generates the corrected second X-ray image by enlarging the second X-ray image on one end side in the direction which is orthogonal to the direction D″ and corresponds to the tilt direction (the direction orthogonal to the conveying direction D) of the second line sensor 15, and reducing on the other end side (see FIG. 14). Also, the corrected-image generation unit 22*d* generates the corrected second X-ray image by enlarging or reducing the second X-ray image in the direction which is orthogonal to the direction D″ and corresponds to the tilt direction (the direction orthogonal to the conveying direction D) of the second line sensor 15 (see FIG. 14).

(4) Characteristics (4-1)

The X-ray inspection device 10 according to the embodiment described above is provided with the conveyor unit 12 as a conveying means, the X-ray emitter 13 as an X-ray source, the first line sensor 14, the second line sensor 15, the detection unit 22*ca*, and the corrected-image generation unit 22*d*. The conveyor unit 12 conveys an article P. The X-ray emitter 13 emits X-rays to the article P conveyed by the conveyor unit 12. The first line sensor 14 detects X-rays that have passed through the article P in a low-energy band. The second line sensor 15 detects X-rays that have passed through the article P in a high-energy band which is different from the low-energy band. The detection unit 22*ca* detects positional displacement of the second line sensor 15 with respect to the first line sensor 14 in the horizontal direction and the vertical direction. The corrected-image generation unit 22*d* generates, based on the detection results of the detection unit 22*ca*, a corrected second X-ray image by correcting the second X-ray image of the article P obtained based on the detection results of the second line sensor 15.

In this configuration, positional displacement of the second line sensor 15 with respect to the first line sensor 14 in the horizontal and vertical direction is detected, and the second X-ray image obtained from the detection results of the second line sensor 15 is corrected based on the displacement. For this reason, accurate inspection results can be obtained even when displacement is occurred in the mounting position of the line sensors 14, 15. In other words, a highly reliable X-ray inspection device 10 being capable of obtaining accurate inspection results is realized regardless of the displacement of the mounting position of the second line sensor 15 with respect to the first line sensor 14.

(4-2)

In the X-ray inspection device 10 according to the embodiment described above, the second line sensor 15 is arranged below the first line sensor 14. A high-energy band as the second energy band is higher than the low-energy band as the first energy band in energy.

In this configuration, because the first line sensor 14 is arranged above the second line sensor 15, articles (obstacles) through which the X-rays from the X-ray emitter 13 pass before reaching the first line sensor 14 is fewer than articles through which the X-rays from the X-ray emitter 13 pass before reaching the second line sensor 15. For this reason, the first X-ray image is a clearer image than the second X-ray image. In this case, because the first X-ray image, which is clearer than the second X-ray image, is used as a reference, positional displacement of the second line sensor 15 with respect to the first line sensor 14 can be readily and accurately obtained.

(4-3)

In the X-ray inspection device 10 according to the embodiment described above, the detection unit 22ca detects positional displacement of the second line sensor 15 with respect to the first line sensor 14 in advance based on the detection result of the first line sensor 14 and the second line sensor 15 of the X-rays which have been emitted from the X-ray emitter 13 to the sample S having a known shape, which is conveyed by the conveyor unit 12, and have passed through the sample S.

In this configuration, the positional displacement of the second line sensor 15 with respect to the first line sensor 14 can be more accurately detected using an X-ray image of a sample S having a known shape.

(4-4)

In the X-ray inspection device 10 according to the embodiment described above, the detection unit 22ca detects the horizontal-direction tilt of the second line sensor 15 with respect to the first line sensor 14. The corrected-image generation unit 22d generates the corrected second X-ray image by rotating the second X-ray image.

In this configuration, a corrected second X-ray image can be generated by correcting the second X-ray image with image processing and accurate inspection results thereby can be obtained, even when horizontal-direction tilt (rotational displacement of the position in the horizontal direction) of the second line sensor 15 with respect to the first line sensor 14 is occurred.

(4-5)

In the X-ray inspection device 10 according to the embodiment described above, the detection unit 22ca detects displacement of the second line sensor 15 with respect to the first line sensor 14 to the upstream side or downstream side in the conveying direction D of the conveyor unit 12. The corrected-image generation unit 22d generates the corrected second X-ray image by moving the second X-ray image in the direction that corresponds to the upstream side or the downstream side of the conveying direction D (the upstream side or downstream side in the direction D").

In this configuration, a corrected second X-ray image can be generated by correcting the second X-ray image with image processing, and accurate inspection results thereby can be obtained, even when displacement of the second line sensor 15 with respect to the first line sensor 14 is occurred to the upstream side or downstream side in the conveying direction D.

(4-6)

In the X-ray inspection device 10 according to the embodiment described above, the detection unit 22ca detects displacement of the second line sensor 15 with respect to the first line sensor 14 in the direction orthogonal to the conveying direction D of the conveyor unit 12 as viewed from above. The corrected-image generation unit 22d generates the corrected second X-ray image by moving the second X-ray image in the direction that corresponds to the direction orthogonal to the conveying direction D (the direction orthogonal to the direction D").

In this configuration, a corrected second X-ray image can be generated by correcting the second X-ray image with image processing and accurate inspection results thereby can be obtained, even when displacement of the second line sensor 15 with respect to the first line sensor 14 is occurred in the direction orthogonal to the conveying direction D.

(4-7)

In the X-ray inspection device 10 according to the embodiment described above, the detection unit 22ca detects the vertical-direction tilt of the second line sensor 15 with respect to the first line sensor 14. The corrected-image generation unit 22d generates the corrected second X-ray image by enlarging the second X-ray image at one end side and reducing the second X-ray image at the other end side in the direction that corresponds to the tilt direction of the second line sensor 15 (in the direction orthogonal to the direction D").

In this configuration, a corrected second X-ray image can be generated by correcting the second X-ray image with image processing and accurate inspection results thereby can be obtained, even when the second line sensor 15 is tilted with respect to the first line sensor 14 in the vertical direction.

(4-8)

In the X-ray inspection device 10 according to the embodiment described above, the detection unit 22ca detects the vertical-direction tilt of the second line sensor 15 with respect to the first line sensor 14. The corrected-image generation unit 22d generates the corrected second X-ray image by enlarging or reducing the second X-ray image in the direction that corresponds to the tilt direction of the second line sensor 15 (in the direction D" or the direction orthogonal to the direction D").

In this configuration, a corrected second X-ray image can be generated by correcting the second X-ray image with image processing and accurate inspection results thereby can be obtained, even when the second line sensor 15 is tilted with respect to the first line sensor 14 in the vertical direction.

(4-9)

In the X-ray inspection device 10 according to the embodiment described above, the detection unit 22ca detects displacement of the second line sensor 15 with respect to the first line sensor 14 in the vertical direction. The corrected-image generation unit 22d generates the corrected second X-ray image by enlarging or reducing the second X-ray image.

In this configuration, a corrected second X-ray image can be generated by correcting the second X-ray image with image processing and accurate inspection results thereby can be obtained, even when the second line sensor 15 is displaced in the vertical direction with respect to the first line sensor 14.

(5) Modifications

Modifications of the above-described embodiment are described below. The following modifications may be combined with other modifications as long as the modifications do not contradict one another.

(5-1) Modification A

A case in which the second line sensor 15 has the positional displacement of any of the patterns (a) to (f) described in (3-1) with respect to the first line sensor 14 is described in the above-described embodiment, but no limitation is imposed thereby. The detection unit 22ca is capable of detecting compound positional displacement of the second line sensor 15 with respect to the first line sensor 14 (a plurality of combination of the patterns (a) to (f)) by combining detection of the positional displacement of patterns (a) to (f). Also, the corrected-image generation unit 22d is capable of generating a corrected second X-ray image in accordance with compound positional displacement of the second line sensor 15 with respect to the first line sensor 14 by performing generating processes of a corrected second X-ray image of the patterns (a) to (f) described in (3-2) together in combination.

(5-2) Modification B

In the embodiment described above, the detection unit 22ca detects the six types of positional displacement of the second line sensor 15 of patterns (a) to (f) described in (3-1), with respect to the first line sensor 14, but no limitation is imposed thereby. For example, when it is known that a certain type of positional displacement is unlikely to occur, the detection unit 22ca may be configured to detect only a portion of the positional displacement among the patterns (a) to (f).

(5-3) Modification C

In the embodiment described above, the first line sensor 14 and second line sensor 15 are disposed vertically in a line, but no limitation is imposed thereby. The X-ray inspection device may have the first line sensor and second line sensor disposed in horizontal positions lined up in the conveying direction D of the conveyor unit 12.

In this case, the second X-ray image generation unit 22b is not required to execute a process in which the X-ray image generated based on the X-ray transmission signals outputted from the X-ray detection elements 15a is reduced by a predetermined factor.

(5-4) Modification D

In the embodiment described above, the detection unit 22ca detects positional displacement of the second line sensor 15 with respect to the first line sensor 14, and the corrected-image generation unit 22d generates a corrected second X-ray image in which the second X-ray image is corrected, but no limitation is imposed thereby. A configuration may be adopted in which the detection unit 22ca detects positional displacement of the first line sensor 14 with respect to the second line sensor 15, and the corrected-image generation unit 22d generates a corrected first X-ray image in which the first X-ray image is corrected.

Because the second line sensor 15 is disposed below the first line sensor 14, it is difficult to obtain a second X-ray image that is clearer than the first X-ray image. In view of this fact, the same configuration as the embodiment described above may be used for the detection unit 22ca even when positional displacement of the first line sensor 14 with respect to the second line sensor 15 is to be detected. When the positional displacement of the second line sensor 15 with respect to the first line sensor 14 is detected, it is possible to detect positional displacement of the first line sensor 14 with respect to the second line sensor 15 simultaneously.

(5-5) Modification E

In the embodiment described above, a flat sheet having rectangular shape as viewed from above is used as the sample S, but the shape of the sample S is not limited thereto. The shape of the sample S may be triangular, ellipsoidal, or other shape as viewed from above.

However, using a rectangular sample S that has sides of differing lengths and the sides intersect at right angles allows positional displacement of the second line sensor 15 with respect to the first line sensor 14 to be detected with particularly good precision.

(5-6) Modification F

In the embodiment described above, positional displacement of the second line sensor 15 with respect to the first line sensor 14 is detected in advance using the sample S, but no limitation is imposed thereby. For example, positional displacement of the second line sensor 15 with respect to the first line sensor 14 may be detected using an article P, which is an article to be inspected. However, the positional displacement of the second line sensor 15 is preferably detected in advance using a sample S when the article P has a circular shape, a complex shape, or other shape as viewed from above that is not a shape suitable for detection of positional displacement of the second line sensor 15.

(5-7) Modification G

In the embodiment described above, the X-ray inspection device 10 inspects the article P for foreign matter, but the type of inspection is not limited to foreign matter inspection; also possible are various inspections using the corrected second X-ray image.

(5-8) Modification H

The method by which positional displacement of the second line sensor 15 is detected by the detection unit 22ca and the method by which the correction parameter is calculated by the calculation unit 22cb as described in the embodiments above are examples, which are not provided by way of limitation. The detection unit 22ca may be configured so as to detect that there is positional displacement of the second line sensor 15 with respect to the first line sensor 14 when the first area A1 and the second area A2 do not overlap, and the calculation unit 22cb may be configured so as to calculate the correction parameter so that the second area A2 exactly overlaps the first area A1.

(5-9) Modification I

In the embodiment described above, it is assumed in the description of the process of the detection unit 22ca that the first line sensor 14 is installed in a designed position, but the same process may be executed even when the first line sensor 14 is displaced from the designed position. In other words, a configuration may be adopted such that, the detection unit 22ca detects that there is positional displacement of the second line sensor 15 with respect to the first line sensor 14 when the first area A1 and the second area A2 do not overlap, and such that the calculation unit 22cb calculates the correction parameter so that the second area A2 exactly overlaps the first area A1.

INDUSTRIAL APPLICABILITY

The X-ray inspection device of certain implementations of the present invention are useful as an X-ray inspection device having high reliability capable of obtaining accurate inspection results even when there is displacement of the mounting position of the two line sensors.

The invention claimed is:

1. An X-ray inspection device comprising:
   a conveying means configured to convey an article;
   an X-ray source configured to emit X-rays to the article conveyed by the conveying means;
   a first line sensor configured to detect, in a first energy band, X-rays that have passed through the article;
   a second line sensor configured to detect, in a second energy band being different from the first energy band, X-rays that have passed through the article;
   a detection unit configured to detect positional displacement of the second line sensor with respect to the first line sensor at least one direction of horizontal direction and vertical direction; and
   a corrected-image generation unit configured to generate, based on the detection results of the detection unit, a corrected second X-ray image by correcting a second X-ray image of the article obtained based on the detection results of the second line sensor.

2. The X-ray inspection device according to claim 1, wherein
   the second line sensor is arranged below the first line sensor, and the second energy band is higher than the first energy band in energy.

3. The X-ray inspection device according to claim 1, wherein
the detection unit is configured to detect positional displacement of the second line sensor with respect to the first line sensor in advance based on the detection result of the first line sensor and the second line sensor of the X-rays which have been emitted from the X-ray source to a sample having a known shape, which is conveyed by the conveying means, and have passed through the sample.

4. The X-ray inspection device according to claim 1, wherein
the detection unit is configured to detect the horizontal-direction tilt of the second line sensor with respect to the first line sensor, and
the corrected-image generation unit is configured to generate the corrected second X-ray image by rotating the second X-ray image.

5. The X-ray inspection device according to claim 1, wherein
the detection unit is configured to detect displacement of the second line sensor with respect to the first line sensor to an upstream side or a downstream side in the conveying direction of the conveying means, and
the corrected-image generation unit is configured to generate the corrected second X-ray image by moving the second X-ray image in a direction that corresponds to the upstream side or the downstream side in the conveying direction.

6. The X-ray inspection device according to claim 1, wherein
the detection unit is configured to detect displacement of the second line sensor with respect to the first line sensor in a direction orthogonal to the conveying direction of the conveying means as viewed from above, and
the corrected-image generation unit is configured to generate the corrected second X-ray image by moving the second X-ray image in a direction that corresponds to the direction orthogonal to the conveying direction.

7. The X-ray inspection device according to claim 1, wherein
the detection unit is configured to detect the vertical-direction tilt of the second line sensor with respect to the first line sensor, and
the corrected-image generation unit is configured to generate the corrected second X-ray image by enlarging the second X-ray image at one end side and reducing the second X-ray image at the other end side in a direction that corresponds to the tilt direction of the second line sensor.

8. The X-ray inspection device according to claim 1, wherein
the detection unit is configured to detect the vertical-direction tilt of the second line sensor with respect to the first line sensor, and
the corrected-image generation unit is configured to generate the corrected second X-ray image by enlarging or reducing the second X-ray image in a direction that corresponds to the tilt direction of the second line sensor.

9. The X-ray inspection device according to claim 1, wherein
the detection unit is configured to detect vertical-direction displacement of the second line sensor with respect to the first line sensor, and
the corrected-image generation unit is configured to generate the corrected second X-ray image by enlarging or reducing the second X-ray image.

* * * * *